US012054790B2

(12) United States Patent
Pagani et al.

(10) Patent No.: US 12,054,790 B2
(45) Date of Patent: Aug. 6, 2024

(54) COMPOSITIONS, METHODS AND KITS FOR MICROORGANISM DETECTION

(71) Applicant: LIFE TECHNOLOGIES CORPORATION, Carlsbad, CA (US)

(72) Inventors: Ioanna Pagani, Oakland, CA (US); Pius Brzoska, Woodside, CA (US); Kelly Li, San Jose, CA (US); Sunali Patel, San Francisco, CA (US); Boli Huang, Palo Alto, CA (US); Kamini Varma, Saratoga, CA (US); Nitin Puri, Pleasanton, CA (US); Evan Diamond, Austin, TX (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 411 days.

(21) Appl. No.: 16/856,036

(22) Filed: Apr. 23, 2020

(65) Prior Publication Data
US 2020/0248239 A1 Aug. 6, 2020

Related U.S. Application Data

(63) Continuation of application No. 15/625,550, filed on Jun. 16, 2017, now abandoned.

(60) Provisional application No. 62/351,843, filed on Jun. 17, 2016, provisional application No. 62/351,226, filed on Jun. 16, 2016.

(51) Int. Cl.
C12Q 1/68 (2018.01)
C12Q 1/6888 (2018.01)
C12Q 1/689 (2018.01)
C12Q 1/6895 (2018.01)

(52) U.S. Cl.
CPC .......... *C12Q 1/689* (2013.01); *C12Q 1/6888* (2013.01); *C12Q 1/6895* (2013.01); *C12Q 2600/158* (2013.01); *C12Q 2600/16* (2013.01)

(58) Field of Classification Search
CPC .... C12Q 1/689; C12Q 1/6888; C12Q 1/6895; C12Q 2600/158; C12Q 2600/16
See application file for complete search history.

(56) References Cited

U.S. PATENT DOCUMENTS

| | | | |
|---|---|---|---|
| 2003/0050470 A1* | 3/2003 | An | C07H 21/00 435/6.14 |
| 2007/0178495 A1* | 8/2007 | Fredricks | C12Q 1/689 435/6.15 |
| 2016/0265031 A1* | 9/2016 | Liu | C12Q 1/6806 |
| 2017/0362640 A1* | 12/2017 | Pagani | C12Q 1/6888 |
| 2018/0073055 A1* | 3/2018 | Pagani | C12Q 1/706 |
| 2020/0248239 A1* | 8/2020 | Pagani | C12Q 1/689 |

FOREIGN PATENT DOCUMENTS

| | | | | |
|---|---|---|---|---|
| CN | 101305101 A | 11/2008 | | |
| CN | 101490275 A | 7/2009 | | |
| CN | 102816857 A | 12/2012 | | |
| WO | WO-2011103274 A1 * | 8/2011 | ............ | C12Q 1/689 |
| WO | WO-2014145870 A2 * | 9/2014 | .......... | C12Q 1/6881 |
| WO | WO-2016095789 A1 | 6/2016 | | |
| WO | WO-2016112252 A1 | 7/2016 | | |

OTHER PUBLICATIONS

Aw et al., 2012. Detection of pathogens in water: from phylochips to qPCR to pyrosequencing. Current opinion in biotechnology, 23(3), pp. 422-430. (Year: 2012).*
Chen et al., 2015. Assembly-line manipulation of droplets in microfluidic platform for fluorescence encoding and simultaneous multiplexed DNA detection. Talanta, 134, pp. 271-277. (Year: 2015).*
Fettweis et al., Vaginal Microbiome Consortium, 2014. Differences in vaginal microbiome in African American women versus women of European ancestry. Microbiology, 160(Pt 10), p. 2272-2282. (Year: 2014).*
Fredricks et al., 2007. Targeted PCR for detection of vaginal bacteria associated with bacterial vaginosis. Journal of clinical microbiology, 45(10), pp. 3270-3276. (Year: 2007).*
Genbank Accession No. AY72474—Uncultured bacterium clone 123-f 23 16S ribosomal RNA gene, partial sequence, submitted Aug. 13, 2004, retrieved on Nov. 14, 2022 from http://www.ncbi.nlm.nih.gov/nuccore/AY724740). (Year: 2004).*
Genbank Accession No. AY738672—Uncultured *Megasphaera* sp. clone 127-Q 35 16S ribosomal RNA gene, partial sequence, submitted Aug. 17, 2004, retrieved on Nov. 14, 2022 from http://www.ncbi.nlm.nih.gov/nuccore/AY738672). (Year: 2004).*
Genbank Accession No. AY738697—Uncultured *Megasphaera* sp. clone 123-Q 3 16S ribosomal RNA gene, partial sequence, submitted Aug. 20, 2004, retrieved on Nov. 14, 2022 from http://www.ncbi.nlm.nih.gov/nuccore/AY738697). (Year: 2004).*
Grigorenko et al., 2014. Multiplex screening for blood-borne viral, bacterial, and protozoan parasites using an OpenArray platform. The Journal of Molecular Diagnostics, 16(1), pp. 136-144. (Year: 2014).*
Ling et al., 2010. Molecular analysis of the diversity of vaginal microbiota associated with bacterial vaginosis. BMC genomics, 11(1), pp. 1-16. (Year: 2010).*
Taly et al., 2012. Detecting biomarkers with microdroplet technology. Trends in molecular medicine, 18(7), pp. 405-416. (Year: 2012).*
Eiderbrant, K., 2011. Master Thesis. Dept of Clinical and Experimental Medicine, Linkopings universitet. Development of quantitative PCR methods for diagnosis of bacterial vaginosis and vaginal yeast infection. pp. 1-59. (Year: 2011).*
Van Doorn et al., 2009. Accurate quantification of microorganisms in PCR-inhibiting environmental DNA extracts by a novel internal amplification control approach using Biotrove OpenArrays. Applied and environmental microbiology, 75(22), pp. 7253-7260. (Year: 2009).*

(Continued)

*Primary Examiner* — Stephanie K Mummert
*Assistant Examiner* — Olayinka A Oyeyemi

(57) ABSTRACT

Methods, compositions and kits for detecting microorganisms and/or profiling microbiota such as for example through use of nucleic acid amplification and detection.

5 Claims, 3 Drawing Sheets

Specification includes a Sequence Listing.

(56) References Cited

OTHER PUBLICATIONS

Genbank Accession No. CP126676.1—Prevotella bivia strain PLW0727 chromosome 1, complete sequence, (submitted May 29, 2023, retrieved on Oct. 1, 2023 from http://www.ncbi.nlm.nih.gov/nuccore/CP126676). (Year: 2023).*
Genbank Accession No. CP126677.1—Prevotella bivia strain PLW0727 chromosome 2, complete sequence, (submitted May 29, 2023, retrieved on Oct. 1, 2023 from http://www.ncbi.nlm.nih.gov/nuccore/CP126677). (Year: 2023).*
Genbank Accession No. CP065631.1—Fannyhessea vaginae strain FDAARGOS_934 chromosome, complete genome, (submitted Dec. 2, 2020, retrieved on Oct. 1, 2023 from http://www.ncbi.nlm.nih.gov/nuccore/CP065631.1). (Year: 2020).*
Genbank Accession No. AF206033.1—Uncultured bacterium clone 123-f 23 16S ribosomal RNA gene, partial sequence, (submitted Nov. 17, 1999, retrieved on Oct. 1, 2023 from http://www.ncbi.nlm.nih.gov/nuccore/AF206033). (Year: 1999).*
Genbank Accession No. AY724740.1—Uncultured bacterium clone 123-f 23 16S ribosomal RNA gene, partial sequence, (submitted Aug. 13, 2004, retrieved on Oct. 1, 2023 from http://www.ncbi.nlm.nih.gov/nuccore/AY724740). (Year: 2004).*
Genbank Accession No. CP002104.1—Gardnerella vaginalis ATCC 14019, complete genome, submitted Jul. 16, 2010, retrieved on Oct. 1, 2023 from http://www.ncbi.nlm.nih.gov/nuccore/CP002104.1). (Year: 2010).*
Genbank Accession No. AY738672.1—Uncultured Megasphaera sp. clone 127-Q 35 16S ribosomal RNA gene, partial sequence, (submitted Aug. 13, 2004, retrieved on Oct. 1, 2023 from http://www.ncbi.nlm.nih.gov/nuccore/AY738672). (Year: 2004).*
Genbank Accession No. AY738697.1—Uncultured Megasphaera sp. clone 123-Q 3 16S ribosomal RNA gene, partial sequence, (submitted Aug. 20, 2004, retrieved on Oct. 1, 2023 from http://www.ncbi.nlm.nih.gov/nuccore/AY738697). (Year: 2004).*
Datcu et al., 2013. Vaginal microbiome in women from Greenland assessed by microscopy and quantitative PCR. BMC infectious diseases, 13, pp. 1-14. (Year: 2013).*
Dols et al., 2011. Microarray-based identification of clinically relevant vaginal bacteria in relation to bacterial vaginosis. American journal of obstetrics and gynecology, 204(4), 305-e1. pp. 1-7. (Year: 2011).*
Hummelen et al., 2010. Deep sequencing of the vaginal microbiota of women with HIV. PloS one, 5(8), e12078, p. 1-9. (Year: 2010).*
Santiago et al. (2012) Longitudinal qPCR study of the dynamics of L. crispatus, L. iners, A. vaginae, (sialidase positive) G. vaginalis, and P. bivia in the vagina. PLoS ONE, 7(9): e45281, pp. 1-9. (Year: 2012).*
AFFYMETRIX: "Affymetrix Data Sheet GeneChip E.Coli Genome 2.0", Retrieved from the Internet: URL:https://assets.thermofisher.com/TFS-Assets/LSG/brochures/ecoli2_datasheet.pdf retrieved on Aug. 24, 2017] , Jan. 1, 2005 , 1-2.
Affymetrix: "Affymetrix E.coli Array 2.0 contains probe for 16s ribosomal RNA", , Jan. 1, 2005 (Jan. 1, 2005 ), XP055400858, Retrieved from the Internet: URL:https://www.affymetrix.com/analysis/netaffx [retrieved on Aug. 24, 2017].
Aroutcheva A, Ling Z, Faro S. Prevotella bivia as a source of lipopolysaccharide in the vagina. Anaerobe. Nov. 2008; 14(5):256-60. Epub Sep. 20, 2008. (Year: 2008).
Datcu R, Gesink D, Mulvad G, Montgomery-Andersen R, RinkE, Koch A, Ahrens P, Jensen JS. Vaginal microbiome in women from Greenland assessed by microscopy and quantitative PCR. BMC Infect Dis. Oct. 16, 2013; 13:480, pp. 1-14 and Table S1. (Year: 2013).
Datcu Table S1-Supporting, 2013, BMC, Oct. 16, 2013 480.
De Backer, et al., "Quantitative determination by real-time PCR of four vaginal Lactobacillus species, Gardnerella vaginalis and Atopobium vaginae indicates an inverse relationship between L. gasseri and L. iners", BMC Microbiology, vol. 7:115, Dec. 19, 2007, pp. 1-13.

E Affymetrix: "Affymetrix E.coli 2 Array contains probe for UreB", Jan. 1, 2005 (Jan. 1, 2005 ), XP055400857, Retrieved from the Internet: URL:https://www.affymetrix.com/analysis/netaffx [retrieved on Aug. 24, 2017].
Einsele, H., et al., "Detection and Identification of Fungal Pathogens in Blood by Using Molecular Probes", Journal of Clinical Microbiology, American Society for Microbiology, US, vol. 35, No. 6, Jun. 1, 1997, 1353-1360.
English Translation of CN 102816857, published Dec. 12, 2012 by Li Xuxin et al. (Year: 2012) pp. 1-43.
Fredricks, et al., "Changes in Vaginal Bacterial Concentrations with Intravaginal Metronidazole Therapy for Bacterial Vaginosis as Assessed by Quantitative PCR", Journal of Clinical Microbiology, vol. 47, No. 3, Mar. 2009, pp. 721-726. Epub Jan. 14, 2009.
GenBank Accession No. AC190685.4, "Zea mays cultivar B73 chromosome 2 clone CH201-167K15, * Sequencing in Progress * , 7 unordered pieces", Submitted by Sep. 24, 2013, https://www.ncbi.nlm.nih.gov/nuccore/AC190685.4/.
GenBank Accession No. BT062642.1, "Zea mays full-length cDNA clone ZM_BFb0326E07 mRNA, complete cds", Submitted by Feb. 21, 2009, https://www.ncbi.nlm.nih.gov/nuccore/BT062642.1/.
Genbank Accession No. CP001849.1, "Gardnerella vaginalis 409-05, complete genome", (submitted Dec. 30, 2009, retrieved Nov. 21, 2019 from http://www.ncbi.nlm.nih.gov/nuccore/CP001849.1).
Genbank Accession No. CP045664.1, "Lactobacillus iners strain LI335 chromosome", (submitted Oct. 2019, retrieved Nov. 21, 2019 from http://www.ncbi.nlm.nih.gov/nuccore/CP045664.1).
GenBank Accession No. CU634002, "Zebrafish DNA sequence from clone CH1073-234E12 in linkage group 17, complete sequence", Submitted by May 15, 2008, https://www.ncbi.nlm.nih.gov/nuccore/CU634002.7/.
Genbank Accession No. EZO72846.1 -hypothetical protein V558_03165 [Pseudomonas aeruginosa BWH057 (submitted by Mar. 18, 2014, retrieved on Jan. 24, 2020 from http://www.ncbi.nlm.nih.gov/nuccore/EZO72846).
Genbank Accession No. FN692037, "Lactobacillus crispatus ST1 complete genome, strain ST1", (submitted Mar. 25, 2010, retrieved Nov. 21, 2019 from http://www.ncbi.nlm.nih.gov/nuccore/FN692037).
GenBank Accession No. HP447215, "TSA: Ictalurus furcatus Contig17922.Icfu mRNA sequence" Submitted by May 6, 2010, https://www.ncbi.nlm.nih.gov/nuccore/HP447215.1/.
Genbank Accession No. JN561323—Human herpesvirus 2 strain HG52, complete genome (submitted by Nov. 1, 2013, retrieved on Nov. 11, 2018 from http://www.ncbi.nlm.nih.gov/nuccore/JN561323), (Year: 2013).
Genbank Accession No. JN867318, "Prevotella bivia strain SEQ245 16S ribosomal RNA gene, partial sequence", Submitted by Oct. 17, 2011, https://www.ncbi.nlm.nih.gov/nuccore/JN867318.1/.
Genbank Accession No. JQ673480.1—Human herpesvirus 1 strain KOS, complete genome (submitted by Feb. 14, 2012, retrieved on Nov. 11, 2018 from http://www.ncbi.nlm.nih.gov/nuccore/JQ673480). (Year: 2012).
GenBank Accession No. JX871274.1, "Uncultured bacterium clone 37.107-2 16S ribosomal RNA gene, partial sequence", Submitted by Sep. 26, 2012, https://www.ncbi.nlm.nih.gov/nuccore/JX871274.1/.
GenBank Accession No. KC018460.1, "Uncultured Deferribacteres bacterium clone F9 16S ribosomal RNA gene, partial sequence", Submitted by Oct. 27, 2012, https://www.ncbi.nlm.nih.gov/nuccore/KC018460.1/.
GenBank Accession No. KF504552.1, "Uncultured Prevotella sp. clone 3922 16S ribosomal RNA gene, partial sequence", Submitted by Aug. 6, 2013, https://www.ncbi.nlm.nih.gov/nuccore/KF504552.1/.
GenBank Accession No. KF999877.1, "Prevotella bivia 16S ribosomal RNA gene, partial sequence", Submitted by Dec. 26, 2013, https://www.ncbi.nlm.nih.gov/nuccore/KF999877.1/.
GenBank Accession No. LK151209.1, "Apteryx australis mantelli genome assembly AptMant0, scaffold C17837902", Submitted by Jun. 1, 2014, https://www.ncbi.nlm.nih.gov/nuccore/LK151209.1/.
GenBank Accession No. LM436768.1, "Nippostrongylus brasiliensis genome assembly, scaffold: NBR_scaffold0003200", Submitted by Jul. 15, 2014, https://www.ncbi.nlm.nih.gov/nuccore/LM436768.1.

(56) References Cited

OTHER PUBLICATIONS

GenBank Accession No. MF087350.1, "Uncultured bacterium clone 134265 16S ribosomal RNA gene, partial sequence", Submitted by May 12, 2017, https://www.ncbi.nlm.nih.gov/nuccore/MF087350.1/.

GenBank Accession No. MF671024.1, "Uncultured *Prevotella* sp. clone CS_595 16S ribosomal RNA gene, partial sequence", Submitted by Aug. 15, 2017, https://www.ncbi.nlm.nih.gov/nuccore/MF671024.1/.

GenBank Accession No. MF895445.1, "Uncultured *Prevotella* sp. clone CSMB_2061 16S ribosomal RNA gene, partial sequence", Submitted by Aug. 28, 2017, https://www.ncbi.nlm.nih.gov/nuccore/MF895445.1/.

GenBank Accession No. MH078461.1, "Uncultured *Prevotella* sp. clone 205_p12_c_36 16S ribosomal RNA gene, partial sequence", Submitted by Mar. 15, 2018, https://www.ncbi.nlm.nih.gov/nuccore/MH078461.1/.

Genbank Accession No. MH152493.1—Uncultured *Prevotella* sp. clone M-p81 16S ribosomal RNA gene, partial sequence (submitted by Mar. 30, 2018, retrieved on Jan. 24, 2020 from http://www.ncbi.nlnn.nih.gov/nuccore/MH152493).

Genbank Accession No. NC_014644.1, "Gardnerella vaginal is ATCC 14019 chromosome, complete genome", (submitted Nov. 3, 2010, retrieved on Nov. 21, 2019 from http://www.ncbi.nlrn.nih.gov/nuccore/NC_014644.1).

Genbank Accession No. NZ_ACGK02000001, "Atopobium vaginae DSM 15829 Contig27.fasta, whole genome shotgun sequence", (submitted Jan. 8, 2009, retrieved Nov. 21, 2019 from http://www.ncbi.nlm.nih.gov/nuccore/NZ_ACGK02000001).

Genbank Accession No. NZ_JH660660, "Prevotella bivia DSM 20514 Prebiscaffold_3, whole genome shotgun sequence", (submitted Feb. 21, 2012, retrieved Nov. 21, 2019 from http://www.ncbi.nlm.nih.gov/nuccore/NZ_JH660660).

Genbank Accession No. U57757—Treponema pallidum Po IA gene, partial cds (GI: 31527 4180, submitted by May 1996, retrieved from http://www.ncbi.nlm.nih.gov/nuccore/U57757). (Year: 1996).

GenBank Accession No. LR535814, "Denticeps clupeoides genome assembly, chromosome: 2", Submitted by Mar. 5, 2019, https://www.ncbi.nlm.nih.gov/nuccore/LR535814.

GenBank Accession No. NZ_GG700801.1, "Lactobacillus iners DSM 13335 SCAFFOLD1", whole genome shotgun sequence, (submitted Apr. 2009, retrieved on Nov. 22, 2019 from the Internet: https://www.ncbi.nlrn.nih.gov/nuccore/NZ_GG700801).

Heymans R., et al., "Clinical Value of Treponema Pallidum Real-Time PCR for Diagnosis of Syphilis," J Clinical Microbial, Feb. 2010; 48(2), pp. 497-502. Epub Dec. 9, 2009. (Year: 2010).

International Preliminary Report on Patentability for International Application No. PCT/US2017/37947 dated Dec. 18, 2018, 12 pages.

Kim, Hwanjung, et al., "The usefulness of multiplex PCR for the identification of bacteria in joint infection", Journal of Clinical Laboratory Analysis, val. 24, No. 3, Jan. 1, 2010, 175-181.

Klingspor, L., et al., "Molecular detection and identification of Candida and Aspergillus spp. from clinical samples using real-time PCR", Clinical Microbiology and Infection, val. 12, No. 8, Aug. 1, 2006, 745-753.

Kusters, et al., "A Multiplex Real-time PCR Assay for Routine Diagnosis of Bacterial Vaginosis", European Journal of Clinical Microbiology & Infectious Diseases, vol. 34, No. 9, Sep. 2015, pp. 1779-1785. Epub Jul. 5, 2015.

Malaguti N, et al., "Sensitive Detection of Thirteen Bacterial Vaginosis-Associated Agents Using Multiplex Polymerase Chain Reaction", BioMed Research International, vol. 2015, 645853, Epub May 20, 2015.

Nadkarni, Mangala, et al., "Determination of bacterial load by real-time PCR using a broad-range (universal) probe and primers set", Microbiology, 148, 2002, 237-266.

Obata-Yasuoka M, et al., "A Multiplex Polymerase Chain Reaction-Based Diagnostic Method for Bacterial Vaginosis", Obstetrics and Gynecology, vol. 100, No. 4, Oct. 2002, pp. 759-764.

PCT/US2017/037947, International Search Report and Written Opinion dated Sep. 18, 2017, 21 pages.

SantaLucia Jr., "PCR Primer Design" Physical principles and visual-OMP software for optimal PCR design, Humana Press, 2007: pp. 3-33. (Year: 2007).

Santiago, et al., "Longitudinal qPCR Study of the Dynamics of L. crispatus, L. iners, A. vaginae, (Sialidase Positive) G.vaginalis, and P. bivia in the Vagina", PLOS One, vol. 7, No. 9, e45281, 2012, pp. 1-9. Epub Sep. 21, 2012.

Vinothkumar, Kittappa, et al., "Triplex PCR assay for the rapid identification of 3 major Vibriospecies, Vibrio cholerae, Vibrio parahaemolyticus, and Vibrio fluvialis", Diagnostic Microbiology and Infectious Disease, val. 76, No. 4, May 22, 2013, 526-528.

Zariffard, Reza, et al., "Detection of bacterial vaginosis-related organisms by real-time PCR for Lactobacilli, Gardnerella vaginalis and Mycoplasma hominis", FEMS Immunology and Medical Microbiology, Elsevier Science B.V., Amsterdam, NL, val. 34, Jan. 1, 2002, 277-281.

Zozaya-Hinchliffe M, et al., "Quantitative PCR Assessments of Bacterial Species in Women with and without Bacterial Vaginosis", Journal of Clinical Microbiology, vol. 48, No. 5, May 2010, pp. 1812-1819, Epub Mar. 19, 2010.

\* cited by examiner

| ATCC gDNA | AVG CRT (N=16) | SD (N=16) |
|---|---|---|
| PB_gDNA_1.0E+03 | 25.09 | 0.23 |
| PB_gDNA_1.0E+04 | 21.76 | 0.12 |
| PB_gDNA_1.0E+05 | 18.28 | 0.20 |
| PB_gDNA_1.0E+06 | 14.74 | 0.08 |

COMPOSITIONS, METHODS AND KITS FOR MICROORGANISM DETECTION

CROSS-REFERENCE TO RELATED APPLICATIONS

This application is a continuation of U.S. application Ser. No. 15/625,550, filed Jun. 16, 2017, which claims the benefit under 35 U.S.C. § 119(e) of U.S. Provisional Application Nos. 62/351,226, filed Jun. 16, 2016 and 62/351,843, filed Jun. 17, 2016. The entire contents of the aforementioned applications are incorporated by reference herein.

FIELD

This disclosure generally relates to the field of molecular biology and genetic analysis, specifically to nucleic acid reagents and to corresponding methods for amplifying, detecting and/or profiling infection causing microorganisms and microbiota.

BACKGROUND

A wide variety of microorganisms can cause or contribute to diseases and disorders. Infectious agents can spread from individual to individual and lead to sickness in the population. Microorganisms which exist on or within a host in a symbiosis can lead to host diseases when imbalances arise in the microbial populations of an individual. The human microbiome project is providing rich insights into the composition of human and animal microbiomes and ability to maintain balance in specific tissues.

Vaginal, urogenital, and urinary tract tissues are rich environments where incidences of bacterial, fungal, viral, and/or parasitic microorganisms can cause imbalance leading to severe impact at the site. For example, imbalance of vaginal flora has been implicated in vaginal infections, which are associated in pre-term birth, infertility, and increased risk of sexually transmitted diseases.

Current technologies for use in vaginal and urinary microbial flora monitoring and detection are costly, lack sensitivity and/or specificity, and/or require a complicated or lengthy workflow. There is a need for methods and systems for assessing and monitoring sensitive, specific, efficient, and cost-effective systems for monitoring and profiling vaginal, urogenital, and urinary tract infection and microbiota.

SUMMARY

Provided herein are methods, compositions, and kits for amplifying a plurality of nucleic acid sequences in a nucleic acid sample, comprising: performing a plurality of amplification reactions in parallel, at least one of the amplification reactions containing a portion of a nucleic acid sample and a pair of amplification primers configured to produce an amplification product (e.g., amplicon) corresponding to the target nucleic acid sequence; forming a plurality of different amplification products; and determining the presence or absence of at least one of the amplification products. In some embodiments, the amplicon comprises a sequence listed in Table 4 (i.e., SEQ ID NOs: 1 through 34). In some embodiments, the target nucleic acid sequence contains a nucleic acid sequence that is identical or complementary to a nucleic acid sequence of a microorganism listed in Table 1. In some embodiments, the target nucleic acid sequence contains a portion of a nucleic acid sequence of a gene listed in Table 2 or its corresponding cDNA.

In another aspect, provided herein are methods, compositions, and kits for detecting the presence of a microorganism nucleic acid in a sample, the method comprising: distributing portions of a nucleic acid sample to individual reaction chambers situated within a support; performing parallel amplification reactions and forming amplification products in the individual reaction chambers, wherein each amplification reaction contains a pair of amplification primers configured to produce an amplification product (e.g., amplicon) corresponding to a target nucleic acid sequence present within, or derived from, the genome of a microorganism, and determining whether an amplification product has been formed in one or more of the individual reaction chambers. In some embodiments, the amplicon comprises a sequence listed in Table 4 (i.e., SEQ ID NOs: 1 through 34). In some embodiments, the target nucleic acid sequence contains a nucleic acid sequence that is identical or complementary to a nucleic acid sequence of a microorganism listed in Table 1. In some embodiments, the target nucleic acid sequence contains a portion of a nucleic acid sequence of a gene listed in Table 2 or its corresponding cDNA.

In another aspect, provided herein are supports for nucleic acid amplification, comprising: a support containing a plurality of reaction sites located within the support or on the support's surface; at least one of the reaction sites containing: (i) a amplification primer pair configured to amplify a corresponding target nucleic acid sequence to produce an amplification product (e.g., amplicon), and (ii) a detectably labeled probe configured to hybridize to a nucleic acid sequence generated by extension of at least one of the amplification primers of the pair. In some embodiments, the amplicon comprises a sequence listed in Table 4 (i.e., SEQ ID NOs: 1 through 34). In some embodiments, the target nucleic acid sequence contains a nucleic acid sequence that is identical or complementary to a nucleic acid sequence of a microorganism listed in Table 1. In some embodiments, the target nucleic acid sequence contains a portion of a nucleic acid sequence of a gene listed in Table 2 or its corresponding cDNA.

In another aspect, provided herein are methods, compositions and kits for the in vitro amplification and detection of at least one target in a sample that is from at least one microorganisms listed in Table 1, comprising: (a) contacting the sample with at least one amplification primer pair, wherein each of the primers comprises a target hybridization region that is configured to produce an amplicon corresponding to the at least one target nucleic acid sequence; (b) performing at least one in vitro amplification reaction under conditions suitable for generating an amplicon corresponding to the at least one target nucleic acid sequence using the primer pair, wherein the amplicon comprises a sequence listed in Table 4 (i.e., SEQ ID NOs:1 through 34); and (c) detecting the amplicon generated in step (b), wherein the detecting comprises contacting the amplicon with a detection probe configured to specifically hybridize to all or a portion of a region of the amplicon. In some embodiments, such methods are for the in vitro amplification and detection of a plurality (e.g., 2, 3, 4, 5, 6, 7, etc.) of different targets in a sample, such as targets from a plurality (e.g., 2, 3, 4, 5, 6, 7, etc.) of different microorganisms listed in Table 1. In some embodiments, the methods produce an amplicon that is between 50 to 300 nucleotides long. In some embodiments, the amplification primer pair and detection probe are components of an assay selected from Table 3.

In another aspect, provided herein methods, compositions, and kits for determining the presence or absence of at least one target nucleic acid from one or more of the microorganisms listed in Table 1 in a biological sample, the composition comprising: (a) at least one amplification primer pair, wherein each of the primers of the pair comprises a target hybridization region that is configured to specifically hybridize to all or a portion of a region of the target nucleic acid and wherein under suitable conditions the primer pair generates an amplicon which comprises a sequence listed in Table 4 (i.e., SEQ ID NOs:1 through 34); and (b) at least one detection probe configured to specifically hybridize to all or a portion of a region of the amplicon produced by the primer pair. In some embodiments, the amplicon is between 50 to 300 nucleotides long. In some embodiments, the at least one amplification primer pair and at least one detection probe are components of an assay selected from Table 3.

In yet other aspects, provided herein are a set of nucleotide probes for detecting a panel of biomarkers, the probes being complementary to DNA and/or RNA sequences of a group of genes; characterized in that the group of genes are selected from any combination of those listed in Table 2. In some embodiments, the set of nucleotide probes are selected from any combination of assays listed in Table 3. In some embodiments, the set of probes comprises 2 to 34 different probes selected from the different assays listed in Table 3.

In yet other aspects, provided herein are methods, compositions and kits for profiling a panel of biomarkers associated with a biological sample comprising: (a) obtaining the biological sample from a subject; (b) contacting at least some portion of the sample with a plurality of individual amplification reactions, each of the individual reactions comprising a set of target-specific primers and a polymerase; (c) amplifying at least one target sequence per individual reaction under conditions able to produce an amplified product; (c) contacting each of the plurality of individual reactions with a detectably labeled probe specific for the amplified product produced by the target-specific primers; (d) determining the presence or absence of the amplified product in each of the plurality of individual amplification reactions to arrive at a biomarker profile for the biological sample. In some embodiments, the biomarkers are associated with vaginal, urogenital, or urinary tract infection and/or microbiota. In some embodiments, the panel comprises a set of 2 to 34 different biomarkers. In some embodiments, the plurality of individual amplification reactions is located on a solid support. In some embodiments, the plurality of individual amplification reactions is located on the same support. In some embodiments, each individual amplification reaction comprises at least one assay selected from Table 3.

In some other aspects, provided herein are methods, compositions and kits for profiling gene expression in a human subject, the method comprising determining, for each gene of a set of genes, a level of RNA encoded by the gene in a biological sample of the subject, wherein the set comprises the genes identified as those listed in Table 3 or any combination thereof. In some embodiments, method comprises amplification and detection of the set of genes using a set of assays selected from those listed in Table 3. In some embodiments, set of genes are derived from any of the microorganisms listed in Table 1. In some embodiments, the method comprises generation of at least one amplification product corresponding to the RNA or DNA encoded by the genes, characterized in that the amplification product comprises a sequence selected from those listed in Table 4. In some embodiments, the set of genes comprises 2 to 34 different genes.

These and other features of the present teachings are provided herein.

BRIEF DESCRIPTION OF THE DRAWINGS

The skilled artisan will understand that the drawings described below, are for illustration purposes only. The drawings are not intended to limit the scope of the present teachings in any way.

DESCRIPTION OF EXEMPLARY EMBODIMENTS

Figure 1:
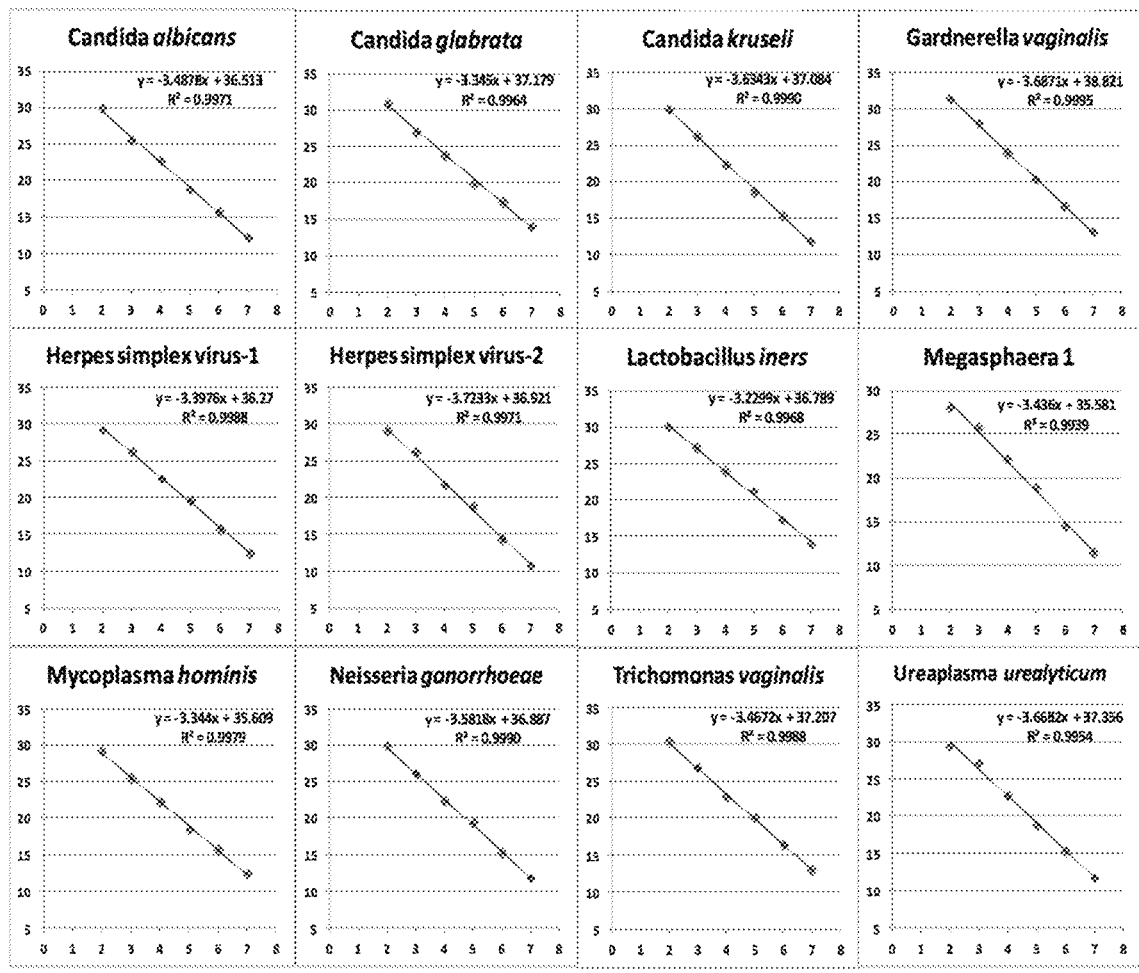
FIG. 1 depicts graphical results for limit of detection and dynamic range for assays directed to a panel of twelve different targets. In each graph, the X-axis shows $\log_{10}$ of the template concentration and the Y-axis shows the PCR Ct values.

In some embodiments, the disclosure relates generally to methods, compositions, and kits for amplification and characterization of select sets of microorganisms in a biological sample. In some embodiments, provided herein are methods, compositions, and kits for the detection and/or profiling microbiota profiles of select tissues and anatomical regions. For example, in some embodiments, provided herein are methods, compositions, and kits for detecting and/or monitoring vaginal, urogenital, and urinary tract microbiome constituents and dynamics.

In some embodiments, the methods, compositions, and kits provided herein are for detection of healthy and pathogenic microorganisms of vaginal and urinary flora, including a range of bacteria, fungi, protozoa, and virus. In some embodiments, the methods, compositions, and kits provided herein are detection of pathogenic microorganisms, including bacteria, fungi, protozoa, and virus, associated with vaginal and urinary microbiota imbalance.

In some embodiments, the methods, compositions, and kits provided herein are of use in detection of pathogens and microbiota associated with bacterial vaginosis, aerobic vaginitis, candidiasis, and/or sexually transmitted disease. Results from the methods and compositions may be of use in determining treatment regimen(s) suitable for the individual from which the examined sample was obtained. The methods and compositions provided may further be used to monitor the microbiota composition and/or dynamics during and after treatment of the individual.

In some embodiments, the methods provided for detecting a microorganism nucleic acid in a sample includes subjecting the sample to multiple individual amplification reactions, each reaction performed with a pair of amplification primers designed to be specific for at least a portion of the target microbe nucleic acid and a detectably labeled probe specific of the target sequence amplified by the primers. The multiple individual amplification reactions generate individual amplification products for each of the microbes for which the amplification primers and detector probe were designed or configured. The microbial profile of the sample is arrived at by determining the presence or absence of the targeted amplification products from the individual amplification reactions.

In some embodiments, detection assays of the methods and compositions provided involve the use of oligonucleotide primers and a detectably labeled probe for amplification and detection of microbial species-specific gene targets.

In some embodiments, the methods and kits include additional amplification reactions and assays which are performed as reference or control reactions and assays. Without limitation, these reference or control reactions and assays can be used in relative quantification applications to assess the adequacy of the biological sample or the nucleic acid sample, to normalize microbial presence, and/or to detect the presence of amplification inhibitors in the biological or nucleic acid sample. Exemplary target nucleic acids for such reference or control assays include, without limitation, prokaryotic 16S rRNA, human RNase P gene DNA, and added exogenous nucleic acid.

In some embodiments, the disclosure relates generally to methods, compositions, and kits for performing a plurality of single-plex nucleic acid amplification reactions under the same assay conditions and/or at substantially the same time.

In some embodiments, the disclosure relates generally to a method for amplifying a plurality of target sequences in a sample comprising contacting at least some portion of the sample with a plurality of target-specific primers as disclosed herein and at least one polymerase under amplification conditions thereby producing at least one amplified target sequence. In some embodiments, the methods for amplifying a plurality of target sequences in a sample comprising contacting at least some portion of the sample with a plurality of target-specific primer pairs as disclosed herein and at least one polymerase under amplification conditions thereby producing at least one amplified target sequence.

In some embodiments, the methods provided comprise contacting at least some portion of the sample with a plurality of target-specific primer and probe sets as disclosed herein and at least one polymerase under amplification conditions thereby producing at least one amplified target sequence and detecting the presence of the at least one amplified target sequence. Each target-specific primer and probe set comprising a forward primer and a reverse primer designed to specifically amplify a target sequence and a detectably labeled probe specific for the nucleic acid amplified by the forward and reverse primers.

In some embodiments, this disclosure relates generally to methods, compositions and kits for detecting, profiling, and monitoring certain sets of target microorganisms in a biological sample. For example, as described herein, an assay was developed to detect the presence of the microorganisms listed in Table 1 in a single sample preparation. In some embodiments, methods and compositions are provided for detection of at least one of the microorganisms listed in Table 1. In some embodiments, methods and compositions are provided for detection of all of the microorganisms listed in Table 1. In some embodiments, methods and compositions are provided for detection of at least one of the gene targets listed in Table 2. In some embodiments, methods and compositions are provided for detection of all of the gene targets listed in Table 2. In some embodiments, methods and compositions are provided for detection of at least one of the microbial genes listed in Table 3. In some embodiments, methods and compositions are provided for detection of all of the microbial genes listed in Table 3. An Applied Biosystems™ TaqMan™ Assay is a combination of an amplification primer pair and a fluorescently labeled probe designed to work in combination to amplify and detect a target nucleic acid. In some embodiments, methods and compositions include at least one of the primer pairs and probes provided in the Applied Biosystems™ TaqMan™ Assays listed in Table 3. In some embodiments, methods and compositions include all of the primer pairs and probes provided in the Applied Biosystems™ TaqMan™ Assays listed in Table 3.

TABLE 1

Microorganisms

| Microorganism Type | Microorganism name |
|---|---|
| Bacteria | *Atopobium vaginae* |
| Bacteria | *Bacteroides fragilis* |
| Bacteria | BVAB2 |
| Bacteria | Chlamydia/*Chlamydia trachomatis* |
| Bacteria | *Enterococcus faecalis* |
| Bacteria | *Escherichia coli* |
| Bacteria | *Gardnerella vaginalis* |
| Bacteria | Chancroid/*Haemophilus ducreyi* |
| Bacteria | *Lactobacillus crispatus* |
| Bacteria | *Lactobacillus gasseri* |
| Bacteria | *Lactobacillus iners* |
| Bacteria | *Lactobacillus jensenii* |
| Bacteria | *Megasphera* 1 |
| Bacteria | *Megasphera* 2 |
| Bacteria | *Mobiluncus curtisii* |
| Bacteria | *Mobiluncus mulieris* |
| Bacteria | *Mycoplasma genitalium* |
| Bacteria | *Mycoplasma hominis* |
| Bacteria | Gonorrhea/*Neisseria gonorrhoeae* |
| Bacteria | *Prevotella bivia* |
| Bacteria | *Staphylococcus aureus* |
| Bacteria | *Streptococcus agalactiae* (Group B Step) |
| Bacteria | *Treponema pallidum* (Syphilis) |
| Bacteria | *Ureaplasma urealyticum* |
| Fungi | *Candida albicans* |
| Fungi | *Candida dubliniensis* |
| Fungi | *Candida glabrata* |
| Fungi | *Candida krusei* |
| Fungi | *Candida lusitaniae* |
| Fungi | *Candida parapsilosis* |
| Fungi | *Candida tropicalis* |
| Protozoa | Trichomonas/*Trichomonas vaginalis* |
| Virus | Herpes simplex virus 1 (HSV1) |
| Virus | Herpes simplex virus 2 (HSV2) |

TABLE 2

Genes
Gene name 50S ribosomal protein L3
DNA polymerase sliding clamp subunit
16S ribosomal RNA
translocated actin-recruiting phosphoprotein
Aminotransferase claim V
Zinc (II) responsive transcriptional activator, MerR family
beta subunit of RNA polymerase
hemoglobin receptor
carbamoyl-phosphate synthase large subunit
LaCOG01543 (Predicted transcriptional regulator)
HMPREF0520_RS00305
guanine permease
tetR family transcriptional regulator
response regulator containing a CheY-like receiver domain and an HTH DNA-binding domain
MG192 = mgpC
MHO_RS00005
NGO0357
peptidyl-prolyl cys-trans isomerase
ribonuclease P RNA TABLE 2-continued Genes Gene name surface interaction protein
DNA-directed DNA polymerase I
UreB
inositol phosphoryl transferase
tubulin 1
tubulin 4
18S ribosomal RNA
SKN7
alpha tubulin 1
virion host shutoff protein
UL41-UL42 intergenic spacer

TABLE 3

Microorganisms, Genes and Assay Numbers

| Microorganism name | Gene name | TaqMan Assay ID Number |
|---|---|---|
| Atopobium vaginae | 50S ribosomal protein L3 | Ba04646222_s1 |
| Bacteroides fragilis | DNA polymerase sliding clamp subunit | Ba04646225_s1 |
| BVAB2 | 16S ribosomal RNA | Ba04646229_s1 |
| Chlamydia/ Chlamydia trachomatis | translocated actin-recruiting phosphoprotein | Ba04646249_s1 |
| Enterococcus faecalis | Aminotransferase claim V | Ba04646247_s1 |
| Escherichia coli | Zinc (II) responsive transcriptional activator, MerR family | Ba04646242_s1 |
| Gardnerella vaginalis | beta subunit of RNA polymerase | Ba04646236_s1 |
| Chancroid/ Haemophilus ducreyi | hemoglobin receptor | Ba04646228_s1 |
| Lactobacillus crispatus | carbamoyl-phosphate synthase large subunit | Ba04646245_s1 |
| Lactobacillus gasseri | LaCOG01543 (Predicted transcriptional regulator) | Ba04646234_s1 |
| Lactobacillus iners | HMPREF0520_RS00305 | Ba04646257_s1 |
| Lactobacillus jensenii | guanine permease | Ba04646258_s1 |
| Megasphera 1 | 16S ribosomal RNA | Ba04646230_s1 |
| Megasphera 2 | 16S ribosomal RNA | Ba04646231_s1 |
| Mobiluncus curtisii | tetR family transcriptional regulator | Ba04646235_s1 |
| Mobiluncus mulieris | response regulator containing a CheY-like receiver domain and an HTH DNA-binding domain | Ba04646246_s1 |
| Mycoplasma genitalium | MG192 = mgpC | Ba04646251_s1 |
| Mycoplasma hominis | MHO_RS00005 | Ba04646255_s1 |
| Gonorrhea/ Neisseria gonorrhoeae | NGO0357 | Ba04646252_s1 |
| Prevotella bivia | peptidyl-prolyl cys-trans isomerase | Ba04646278_s1 |
| Staphylococcus aureus | ribonuclease P RNA | Ba04646259_s1 |
| Streptococcus agalactiae (Group B Strep) | surface interaction protein | Ba04646276_s1 |
| Treponema pallidum (Syphilis) | DNA-directed DNA polymerase I | Ba04646237_s1 |
| Ureaplasma urealyticum | UreB | Ba04646254_s1 |
| Candida albicans | inositol phosphoryl transferase | Fn04646233_s1 |
| Candida dubliniensis | tubulin 1 | Fn04646244_s1 |
| Candida glabrata | tubulin 4 | Fn04646240_s1 |
| Candida krusei | 18S ribosomal RNA | Fn04646250_s1 |
| Candida lusitaniae | SKN7 | Fn04646241_s1 |
| Candida parapsilosis | tubulin 4 | Fn04646221_s1 |
| Candida tropicalis | tubulin 4 | Fn04646220_s1 |

TABLE 3-continued

Microorganisms, Genes and Assay Numbers

| Microorganism name | Gene name | TaqMan Assay ID Number |
|---|---|---|
| Trichomonas/ Trichomonas vaginalis | alpha tubulin 1 | Pr04646256_s1 |
| Herpes simplex virus 1 (HSV1) | virion host shutoff protein | Vi04230116_s1 |
| Herpes simplex virus 2 (HSV2) | UL41-UL42 intergenic spacer | Vi04646232_s1 |

TABLE 4

Microorganisms and Amplicon-associated Sequences

| Microorganism name | Sequence | SEQ ID NO. |
|---|---|---|
| Atopobium vaginae | GAGCGTGTAACTGTTAAA | 1 |
| Bacteroides fragilis | TTTGCATAATGAATCTGA | 2 |
| BVAB2 | AAGTGTGATGTTTAAATC | 3 |
| Chlamydia/ Chlamydia trachomatis | GACAAGAATGCCTCTGTC | 4 |
| Enterococcus faecalis | GCCTGTTGAAATCGCAAT | 5 |
| Escherichia coli | AGCGATTGAAATTTATCC | 6 |
| Gardnerella vaginalis | GGTGACCTTCATCGTGCT | 7 |
| Chancroid/ Haemophilus ducreyi | TAGGCTATCAATTAAATG | 8 |
| Lactobacillus crispatus | AGTTGCTATCGGTTATCG | 9 |
| Lactobacillus gasseri | AGTTGCTATCGGTTATCG | 10 |
| Lactobacillus iners | AGGTTTTTATCATCCTT | 11 |
| Lactobacillus jensenii | GTTATATGTTATTTGTTG | 12 |
| Megasphera 1 | GGCGTAAAGGGCGCGCAG | 13 |
| Megasphera 2 | ACGGGACGAACGGCAAGG | 14 |
| Mobiluncus curtisii | ACATCTGTTCCAAAATCT | 15 |
| Mobiluncus mulieris | ACTTGTTGGGGATACTTA | 16 |
| Mycoplasma genitalium | ACTTCCATTCCAAATCTT | 17 |
| Mycoplasma hominis | TGAATTCTTTGTTAGAAA | 18 |
| Gonorrhea/ Neisseria gonorrhoeae | GAAGTAAAACTGTATTAC | 19 |
| Prevotella bivia | GGCAACGGTGGCTTAGTG | 20 |
| Staphylococcus aureus | GTATAAACGAGACACACT | 21 |
| Streptococcus agalactiae (Group B Strep) | GAAACAGATACGACGTGG | 22 |
| Treponema pallidum (Syphilis) | GTGAACTCCGTATTGAAG | 23 |
| Ureaplasma urealyticum | TTTGATGATCCTGACATA | 24 |
| Candida albicans | GTGGAGTTTTAACTCATT | 25 |
| Candida dubliniensis | AAACTGATGGCGATTATG | 26 |
| Candida glabrata | CCACCACAACTTCAGATT | 27 |
| Candida krusei | TTCAGGGACGCTTGGCGG | 28 |
| Candida lusitaniae | GTCGAACTGATGGTGGCC | 29 |
| Candida parapsilosis | AGATGGAACACCAACACT | 30 |
| Candida tropicalis | GTGATACATGGTAAGAAA | 31 |
| Trichomonas/ Trichomonas vaginalis | GCTGCTGAATCAGTCGAA | 32 |
| Herpes simplex virus 1 (HSV1) | ACAGGAGGTCAGTGTCTG | 33 |
| Herpes simplex virus 2 (HSV2) | CGGGATAGCGTCTTGTTG | 34 |

In some embodiments, provided are panels of amplification primer pairs specific for selected microorganisms. In some embodiments, provided are panels of amplification primer pairs and corresponding detectably labeled probes, where each primer/probe combination is specific for a selected microorganism. In some embodiments, the microbe panel includes at least one microorganism listed in Table 1. In some embodiments, the microbe panel includes *Prevotella bivia* and at least one other microorganism listed in Table 1. In some embodiments, the microbe panel, independent of reaction, extraction, and/or other control targets, comprises primer pairs specific for at least one of the microorganisms listed in Table 1. In some embodiments, the microbe panel, independent of reaction, extraction, and/or other control targets, comprises primer pairs specific for all of the microorganisms listed in Table 1. In some embodiments, the microbe panel, independent of reaction, extraction, and/or other control targets, consists of primer pairs specific for all of the microorganisms listed in Table 1. In certain embodiments, any of these panels comprise a detectably labeled probe corresponding to the amplification primer pair.

In some embodiments, provided are panels of amplification primer pairs specific for target genes. In some embodiments, provided are panels of amplification primer pairs and corresponding detectably labeled probes, where each primer/probe combination is specific for a target gene. In some embodiments, the gene panel includes at least one genes listed in Table 2. In some embodiments, the gene panel, independent of reaction, extraction, and/or other control targets, comprises primer pairs specific for at least one of the genes listed in Table 2. In some embodiments, the gene panel, independent of reaction, extraction, and/or other control targets, comprises primer pairs specific for all of the genes listed in Table 2. In some embodiments, the gene panel, independent of reaction, extraction, and/or other control targets, consists of primer pairs specific for all of the genes listed in Table 2. In certain embodiments, any of these panels comprise a detectably labeled probe corresponding to the amplification primer pair.

In some embodiments, provided are panels of amplification primer pairs specific for microbial gene targets. In some embodiments, provided are panels of amplification primer pairs and corresponding detectably labeled probes, where each primer/probe combination is specific for a microbial gene target. In some embodiments, the microbial gene panel includes at least one of the microbial genes listed in Table 3. In some embodiments, the microbial gene panel includes *Prevotella bivia* peptidyl-prolyl cys-trans isomerase and at least one other of the microbial genes listed in Table 3. In some embodiments, the microbial gene panel, independent of reaction, extraction, and/or other control targets, comprises primer pairs specific for at least one of the microbial genes listed in Table 3. In some embodiments, the microbial gene panel, independent of reaction, extraction, and/or other control targets, comprises primer pairs specific for all of the microbial genes listed in Table 3. In some embodiments, the microbial gene panel, independent of reaction, extraction, and/or other control targets, consists of primer pairs specific for all of the microbial genes listed in Table 3. In certain embodiments, any of these panels comprise a detectably labeled probe corresponding to the amplification primer pair.

The type or presence of a microorganism in a biological sample can be identified or determined by analyzing nucleic acid prepared from the sample. Once obtained or collected from a source, for example a subject or patient, a biological sample can be processed according to known methods to extract nucleic acids present in the sample. In other instances, a total nucleic acid sample can be prepared from the biological sample. In some instances, steps to enrich microorganisms in the biological sample may be taken prior to nucleic acid extraction. The nucleic acid sample is amplified and analyzed according to known methods, such as polymerase chain reaction (PCR).

When applying quantitative methods to PCR-based technologies, a fluorescent probe or other detectable label may be incorporated into the reaction to provide a means for determining the progress of the target amplification. In the case of a fluorescent probe, the reaction can be made to fluoresce in relative proportion to the quantity of nucleic acid product produced. As such, using PCR, assays for nucleotides sequences corresponding to the microorganism genes are the target sequences and are used to determine the presence or absence of microorganism in or the microbial profile of the biological sample.

In some embodiments, the amplification reactions occur on a support having a plurality of reaction sites and each reaction site contains one pair of amplification primers. In some embodiments, the amplification reactions occur in reaction vessels and each reaction contains one pair of amplification primers. In some embodiments, the reaction vessel further contains at least one target specific oligonucleotide probe, the probe being specific for nucleic acid portion amplified by the amplification primer pair present in the reaction vessel. In certain embodiments, the reaction vessels are through-holes in a support plate and each through-hole contains one pair of amplification primers and at least one detectably-labeled probe as described herein. In some embodiments, the primers or primers and probes are dried in each reaction site or reaction vessel. In some embodiments, a plurality of reaction vessels can reside on the same support.

In some embodiments the support provides a surface for the immobilization, attachment, or placement of amplification reagents (e.g., oligonucleotides, such as probes and/or primers), by any available method so that they are significantly or entirely prevented from diffusing freely or moving with respect to one another. The reagents can, for example, be placed in contact with the support, and optionally covalently or noncovalently attached or partially/completed embedded. Suitable supports are available commercially, and will be apparent to the skilled person. In some embodiments, a solid support can be used for the methods, compositions and kits described herein. Such solid supports can include, but are not limited to, paper, nitrocellulose, myelin, glass, silica, nylon, plastics such as polyethylene, polypropylene or polystyrene, or other solid material. In addition, in some embodiments, the support can be a gel constructed from such materials such as agarose, polyacrylamide, polysaccharide or proteins, which may themselves be overlaid on a further solid surface such as glass or metal, to provide mechanical strength, electrical conductivity or other desired physical property. In certain embodiments, the support may comprise a flat (planar) surface, or at least a structure in which the surface-bound oligonucleotides are attached in approximately the same plane. In other embodiments, the solid support may be non-planar and may even be formed from a plurality of discrete units, e.g. microbeads.

As used herein, the term "surface" means any generally two-dimensional structure on a solid support to which the desired oligonucleotide(s) is/are attached or immobilized.

The amplification reaction vessel can also contain other component reagents of the amplification reaction mixture such as, for example, dNTPs (dATP, dCTP, dGTP and/or dTTP), polymerase, buffer(s), salt(s), detergent(s), amplification inhibitor blocking agent(s), and/or antifoam agent(s). Accordingly, in some embodiments, semi-solid or solid supports are provided with reaction sites or reaction vessels comprising an amplification primer pair together with an amplification reaction mixture or master mix. In some embodiments, the primer pair and reaction mix combination in the reaction site or reaction vessel is dried. In some embodiments, the primer pair and reaction mix combination in the reaction site or reaction vessel is lyophilized and is applied to the reaction site or vessel as a dried deposit. In some embodiments, semi-solid or solid supports are provided with reaction sites or reaction vessels comprising an amplification primer pair and detectably labeled probe together with an amplification reaction mixture or master mix. In some embodiments, the primer pair, probe, and reaction mix combination in the reaction site or reaction vessel is dried. In some embodiments, the primer pair, probe and reaction mix combination in the reaction site or reaction vessel is lyophilized.

In some embodiments, supports are provided comprising a reaction site or reaction vessel comprising a primer or a primer pair specific for at least one of the microorganisms listed in Table 1. In some embodiments, supports are provided comprising a reaction site or reaction vessel comprising a primer or a primer pair specific for *Prevotella bivia*. In some embodiments, supports are provided comprising a plurality of reaction sites or reaction vessels where a reaction site or reaction vessel comprises a primer or a primer pair specific for at least one of the microorganisms listed in Table 1. In some embodiments, supports are provided comprising a plurality of reaction sites or reaction vessels where a reaction site or reaction vessel comprises a primer or a primer pair specific for *Prevotella bivia* and at least one other of the microorganisms listed in Table 1. In some embodiments, supports are provided comprising a plurality of reaction sites or reaction vessels where a reaction site or reaction vessel comprises a primer or a primer pair specific for all of the microorganisms listed in Table 1. In some embodiments, supports are provided comprising a plurality of reaction sites or reaction vessels where a reaction site or reaction vessel comprises a primer or a primer pair specific for at least 10, 11, 12, 13, 14, 15, 16, 17, 18, 19, 20, 21, 22, 23, 24, 25, 26, 27, 28, 29, 30, 31, 32, or 33 of the microorganisms listed in Table 1. In some embodiments, the supports provided further comprise a reaction site or reaction vessel comprising a primer or a primer pair specific for at least 1, 2, 3, 4, 5, 6, 7, 8, 9, or 10 internal and/or external controls.

In some embodiments, supports are provided comprising a reaction site or reaction vessel comprising a primer or a primer pair and a detectably labeled probe each specific for at least one of the microorganisms listed in Table 1. In some embodiments, supports are provided comprising a reaction site or reaction vessel comprising a primer or a primer pair and a detectably labeled probe each specific for *Prevotella bivia*. In some embodiments, supports are provided comprising a plurality of reaction sites or reaction vessels where a reaction site or reaction vessel comprises a primer or a primer pair and a detectably labeled probe each specific for at least one of the microorganisms listed in Table 1. In some embodiments, supports are provided comprising a plurality of reaction sites or reaction vessels where a reaction site or reaction vessel comprises a primer or a primer pair and a detectably labeled probe each specific for *Prevotella bivia* and at least one other of the microorganisms listed in Table 1. In some embodiments, supports are provided comprising a plurality of reaction sites or reaction vessels where a reaction site or reaction vessel comprises a primer or primer pair and a detectably labeled probe each specific for all of the microorganisms listed in Table 1. In some embodiments, supports are provided comprising a plurality of reaction sites or reaction vessels where a reaction site or reaction vessel comprises a primer or a primer pair and a detectably labeled probe each specific for at least 10, 11, 12, 13, 14, 15, 16, 17, 18, 19, 20, 21, 22, 23, 24, 25, 26, 27, 28, 29, 30, 31, 32, or 33 of the microorganisms listed in Table 1. In some embodiments, the supports provided further comprise a reaction site or reaction vessel comprising a primer or a primer pair and a detectably labeled probe each specific for at least 1, 2, 3, 4, 5, 6, 7, 8, 9, or 10 internal and/or external controls.

In some embodiments, supports are provided comprising a reaction site or reaction vessel comprising a primer or a primer pair specific for at least one of the genes listed in Table 2. In some embodiments, supports are provided comprising a plurality of reaction sites or reaction vessels where a reaction site or reaction vessel comprises a primer or a primer pair specific for at least one of the genes listed in Table 2. In some embodiments, supports are provided comprising a plurality of reaction sites or reaction vessels where a reaction site or reaction vessel comprises a primer or a primer pair specific for all of the genes listed in Table 2. In some embodiments, supports are provided comprising a plurality of reaction sites or reaction vessels where a reaction site or reaction vessel comprises a primer or a primer pair specific for at least 10, 11, 12, 13, 14, 15, 16, 17, 18, 19, 20, 21, 22, 23, 24, 25, 26, 27, 28, 29, or 30 of the genes listed in Table 2. In some embodiments, the supports provided further comprise a reaction site or reaction vessel comprising a primer or a primer pair specific for at least 1, 2, 3, 4, 5, 6, 7, 8, 9, or 10 internal and/or external controls.

In some embodiments, supports are provided comprising a reaction site or reaction vessel comprising a primer or a primer pair and a detectably labeled probe each specific for at least one of the genes listed in Table 2. In some embodiments, supports are provided comprising a plurality of reaction sites or reaction vessels where a reaction site or reaction vessel comprises a primer or a primer pair and a detectably labeled probe each specific for at least one of the genes listed in Table 2. In some embodiments, supports are provided comprising a plurality of reaction sites or reaction vessels where a reaction site or reaction vessel comprises a primer or primer pair and a detectably labeled probe each specific for all of the genes listed in Table 2. In some embodiments, supports are provided comprising a plurality of reaction sites or reaction vessels where a reaction site or reaction vessel comprises a primer or a primer pair and a detectably labeled probe each specific for at least 10, 11, 12, 13, 14, 15, 16, 17, 18, 19, 20, 21, 22, 23, 24, 25, 26, 27, 28, 29, or 30 of the genes listed in Table 2. In some embodiments, the supports provided further comprise a reaction site or reaction vessel comprising a primer or a primer pair and a detectably labeled probe each specific for at least 1, 2, 3, 4, 5, 6, 7, 8, 9, or 10 internal and/or external controls.

In some embodiments, supports are provided comprising a reaction site or reaction vessel comprising a primer or a primer pair specific for at least one of the microbial genes listed in Table 3. In some embodiments, supports are provided comprising a reaction site or reaction vessel comprising a primer or a primer pair specific for *Prevotella bivia* peptidyl-prolyl cys-trans isomerase. In some embodiments, supports are provided comprising a plurality of reaction sites or reaction vessels where a reaction site or reaction vessel comprises a primer or a primer pair specific for at least one of the microbial genes listed in Table 3. In some embodiments, supports are provided comprising a plurality of reaction sites or reaction vessels where a reaction site or reaction vessel comprises a primer or a primer pair specific for *Prevotella bivia* peptidyl-prolyl cys-trans isomerase and at least one other of the microbial genes listed in Table 3. In some embodiments, supports are provided comprising a plurality of reaction sites or reaction vessels where a reaction site or reaction vessel comprises a primer or a primer pair specific for all of the microbial genes listed in Table 3. In some embodiments, supports are provided comprising a plurality of reaction sites or reaction vessels where a reaction site or reaction vessel comprises a primer or a primer pair specific for at least 10, 11, 12, 13, 14, 15, 16, 17, 18, 19, 20, 21, 22, 23, 24, 25, 26, 27, 28, 29, 30, 31, 32, or 33 of the microbial genes listed in Table 3. In some embodiments, the supports provided further comprise a reaction site or reaction vessel comprising a primer or a primer pair specific for at least 1, 2, 3, 4, 5, 6, 7, 8, 9, or 10 internal and/or external controls.

In some embodiments, supports are provided comprising a reaction site or reaction vessel comprising a primer or a primer pair and a detectably labeled probe each specific for at least one of the microbial genes listed in Table 3. In some embodiments, supports are provided comprising a reaction site or reaction vessel comprising a primer or a primer pair and a detectably labeled probe each specific for *Prevotella bivia* peptidyl-prolyl cys-trans isomerase. In some embodiments, supports are provided comprising a plurality of reaction sites or reaction vessels where a reaction site or reaction vessel comprises a primer or a primer pair and a detectably labeled probe each specific for at least one of the microbial genes listed in Table 3. In some embodiments, supports are provided comprising a plurality of reaction sites or reaction vessels where a reaction site or reaction vessel comprises a primer or a primer pair and a detectably labeled probe each specific for *Prevotella bivia* peptidyl-prolyl cys-trans isomerase and at least one other of the microbial genes listed in Table 3. In some embodiments, supports are provided comprising a plurality of reaction sites or reaction vessels where a reaction site or reaction vessel comprises a primer or primer pair and a detectably labeled probe each specific for all of the microbial genes listed in Table 3. In some embodiments, supports are provided comprising a plurality of reaction sites or reaction vessels where a reaction site or reaction vessel comprises a primer or a primer pair and a detectably labeled probe each specific for at least 10, 11, 12, 13, 14, 15, 16, 17, 18, 19, 20, 21, 22, 23, 24, 25, 26, 27, 28, 29, 30, 31, 32, or 33 of the microbial genes listed in Table 3. In some embodiments, the supports provided further comprise a reaction site or reaction vessel comprising a primer or a primer pair and a detectably labeled probe each specific for at least 1, 2, 3, 4, 5, 6, 7, 8, 9, or 10 internal and/or external controls.

To more clearly and concisely describe and point out the subject matter of the present disclosure, the following definitions are provided for specific terms, which are used in the following description and the appended claims. Throughout the specification, exemplification of specific terms should be considered as non-limiting examples.

As used in this specification, the words "a" or "an" means at least one, unless specifically stated otherwise. In this specification, the use of the singular includes the plural unless specifically stated otherwise. For example, but not as a limitation, "a target nucleic acid" means that more than one target nucleic acid can be present; for example, one or more copies of a particular target nucleic acid species, as well as two or more different species of target nucleic acid. The term "and/or" means that the terms before and after the slash can be taken together or separately. For illustration purposes, but not as a limitation, "X and/or Y" can mean "X" or "Y" or "X" and "Y".

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting.

It is to be understood that both the foregoing general description and detailed description are exemplary and explanatory only and are not restrictive of the teachings.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

As used herein, the terms "amplification", "nucleic acid amplification", or "amplifying" refer to the production of multiple copies of a nucleic acid template, or the production of multiple nucleic acid sequence copies that are complementary to the nucleic acid template. The terms (including the term "polymerizing") may also refer to extending a nucleic acid template (e.g., by polymerization). The amplification reaction may be a polymerase-mediated extension reaction such as, for example, a polymerase chain reaction (PCR). However, any of the known amplification reactions may be suitable for use as described herein. The term "amplifying" that typically refers to an "exponential" increase in target nucleic acid may be used herein to describe both linear and exponential increases in the numbers of a select target sequence of nucleic acid.

The terms "amplicon" and "amplification product" as used herein generally refer to the product of an amplification reaction. An amplicon may be double-stranded or single-stranded, and may include the separated component strands obtained by denaturing a double-stranded amplification product. In certain embodiments, the amplicon of one amplification cycle can serve as a template in a subsequent amplification cycle.

The terms "annealing" and "hybridizing", including, without limitation, variations of the root words "hybridize" and "anneal", are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers and probes anneal to complementary sequences are well known in the art, e.g., as described in *Nucleic Acid Hybridization, A Practical Approach*, Hames and Higgins, eds., IRL Press, Washington, D.C. (1985) and Wetmur and Davidson, *Mol. Biol.* 31:349 (1968).

In general, whether such annealing takes place is influenced by, among other things, the length of the complementary portions of the complementary portions of the primers and their corresponding binding sites in the target flanking sequences and/or amplicons, or the corresponding complementary portions of a reporter probe and its binding site; the pH; the temperature; the presence of mono- and divalent cations; the proportion of G and C nucleotides in the hybridizing region; the viscosity of the medium; and the presence of denaturants. Such variables influence the time required for hybridization. Thus, the preferred annealing conditions will depend upon the particular application. Such conditions, however, can be routinely determined by persons of ordinary skill in the art, without undue experimentation. Preferably, annealing conditions are selected to allow the primers and/or probes to selectively hybridize with a complementary sequence in the corresponding target flanking sequence or amplicon, but not hybridize to any significant degree to different target nucleic acids or non-target sequences in the reaction composition at the second reaction temperature. In some embodiments, the amplicons of the methods, compositions and kits as described herein, comprise a sequence listed in Table 4 or the complement thereof. In some embodiments, such amplicon-associated sequences listed in Table 4 are at the 5'-end, 3'-end or at an internal location of the amplicon sequence that is produced as a result of amplification. In some embodiments, the amplicon-associated sequences listed in Table 4 can be used to differentiate among a plurality of amplicon sequences produced with regard to the corresponding microorganisms listed for each sequence in Table 4. In some embodiments, the amplicon-associated sequences listed in Table 4 are only a portion of the complete amplicon sequence generated using a corresponding assay listed for the corresponding microorganism listed in Tables 3.

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The terms "denaturing" and "denaturation" as used herein refer to any process in which a double-stranded polynucleotide, including without limitation, a genomic DNA (gDNA) fragment comprising at least one target nucleic acid, a double-stranded amplicon, or a polynucleotide comprising at least one double-stranded segment is converted to two single-stranded polynucleotides or to a single-stranded or substantially single-stranded polynucleotide, as appropriate. Denaturing a double-stranded polynucleotide includes, without limitation, a variety of thermal and chemical techniques which render a double-stranded nucleic acid single-stranded or substantially single-stranded, for example but not limited to, releasing the two individual single-stranded components of a double-stranded polynucleotide or a duplex comprising two oligonucleotides. Those in the art will appreciate that the denaturing technique employed is generally not limiting unless it substantially interferes with a subsequent annealing or enzymatic step of an amplification reaction, or in certain methods, the detection of a fluorescent signal.

As used herein, the term "Tm" is used in reference to melting temperature. The melting temperature is the temperature at which a population of double-stranded nucleic acid molecules becomes half dissociated into single strands.

The term "minor groove binder" as used herein refers to a small molecule that fits into the minor groove of double-stranded DNA, sometimes in a sequence specific manner. Generally, minor groove binders are long, flat molecules that can adopt a crescent-like shape and thus, fit snugly into the minor groove of a double helix, often displacing water. Minor groove binding molecules typically comprise several aromatic rings connected by bonds with torsional freedom, for example, but not limited to, furan, benzene, or pyrrole rings.

The term "end-point" measurement refers to a method where data collection occurs only once the reaction has been stopped.

The terms "real-time" and "real-time continuous" are interchangeable and refer to a method where data collection occurs through periodic monitoring during the course of the polymerization reaction. Thus, the methods combine amplification and detection into a single step.

As used herein the terms "$C_t$," and "cycle threshold" refer to the time at which fluorescence intensity is greater than background fluorescence. They are characterized by the point in time (or PCR cycle) where the target amplification is first detected. Consequently, the greater the quantity of target DNA in the starting material, the faster a significant increase in fluorescent signal will appear, yielding a lower $C_t$.

As used herein, the term "primer" and its derivatives refer generally to any polynucleotide that can hybridize to a target nucleic acid. In some embodiments, the primer can also serve to prime nucleic acid synthesis. In some embodiments, the primer is a synthetically or biologically produced single-stranded oligonucleotide that is extended by covalent bonding of nucleotide monomers during amplification or polymerization of a nucleic acid molecule. Nucleic acid amplification often is based on nucleic acid synthesis by a nucleic acid polymerase or reverse transcriptase. Many such polymerases or reverse transcriptases require the presence of a primer that may be extended to initiate such nucleic acid synthesis. A primer is typically about 11 bases to about 35 bases in length, although shorter or longer primers may be used depending on the need. In certain embodiments, a primer is 17 bases or longer. In certain embodiments, a primer is about 17 bases to about 25 bases in length. A primer may comprise standard, non-standard, derivatized and modified nucleotides. As will be appreciated by those skilled in the art, the oligonucleotides disclosed herein may be used as one or more primers in various extension, synthesis, or amplification reactions.

Typically, a PCR reaction employs a pair of amplification primers including an "upstream" or "forward" primer and a "downstream" or "reverse" primer, which delimit a region of the RNA or DNA to be amplified. A first primer and a second primer may be either a forward or reverse primer and are used interchangeably herein and are not to be limiting.

The terms "complementarity" and "complementary" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementarity refers to the situation in which each nucleotide unit of one polynucleotide strand or region can hydrogen bond with each nucleotide unit of a second polynucleotide strand or region. "Less than perfect complementarity" refers to the situation in which some, but not all, nucleotide units of two strands or two units can hydrogen bond with each other.

As used herein, the term "reverse complement" refers to a sequence that will anneal/base pair or substantially anneal/base pair to a second oligonucleotide according to the rules defined by Watson-Crick base pairing and the antiparallel nature of the DNA-DNA, RNA-RNA, and RNA-DNA double helices. Thus, as an example, the reverse complement of the RNA sequence 5'-AAUUGC would be 5'-GCAAAUU. Alternative base pairing schemes, including but not limited to G-U pairing, can also be included in reverse complements.

As used herein, the term "probe" refers to synthetic or biologically produced nucleic acids (DNA or RNA) which, by design or selection, contain specific nucleotide sequences that allow them to hybridize, under defined stringencies, specifically (i.e., preferentially) to target nucleic acid sequences.

"Biological sample" includes cells, sections of tissues such as biopsy and autopsy samples, and frozen sections taken for histologic purposes, as well as fluid or secretion specimens that arise from cells or tissues. Such samples include blood and blood fractions or products (e.g., serum, platelets, red blood cells, and the like), lymph, bone marrow, sputum, bronchoalveolar lavage, amniotic fluid, hair, skin, cultured cells, e.g., primary cultures, explants, and transformed cells, stool, urine, etc. Prior to target nucleic acid preparation, biological samples may be fresh, frozen or formalin- or paraformalin-fixed paraffin-embedded tissue (FFPE). In some embodiments, a biological sample is from the vagina, vaginal mucosa, vaginal area, urinary tract, or urogenital area and includes cells, tissue and/or fluids (e.g., vaginal secretions, urinary secretions, and anal secretions) from these anatomical sites.

A "biopsy" refers to the process of removing a tissue sample for diagnostic or prognostic evaluation, and to the tissue specimen itself. Any biopsy technique known in the art can be applied to the methods provided herein. The biopsy technique applied will depend on the tissue type to be evaluated (e.g., skin, mucosa, etc.), the size and type of the tissue sample, among other factors. Representative biopsy techniques include, but are not limited to, excisional biopsy, incisional biopsy, needle biopsy, and surgical biopsy.

Samples from the skin, mucosa, or their secretions may be collected using a swab, brush, or scraping tool. Collection systems and media compatible with vaginal or urogenital biological samples are known in the art. Exemplary collection systems and media for such sample types include, but are not limited to, ThinPrep™ Pap test (Hologic Corp.), BD SurePath™ test (Becton, Dickinson and Company), ESwab™ (Copan Diagnostics), Aptima™ Vaginal Swab transport Media (STM) (Hologic), and M4™ MicroTest (Remel), Affirm Ambient Temperature Transport System (Becton, Dickinson and Company), and BD ProbeTec™ Swab diluent Q (Becton, Dickinson and Company).

As used herein, the term "template" is interchangeable with "target molecule" or "target nucleic acid" and refers to a double-stranded or single-stranded nucleic acid molecule which is to be amplified, copied or extended, synthesized, or sequenced. In the case of a double-stranded DNA molecule, denaturation of its strands to form a first and a second strand is performed to amplify, sequence, or synthesize these molecules. Target nucleic acids can include the nucleic acid sequences to which primers useful in the amplification or synthesis reaction can hybridize prior to extension by a polymerase. A primer, complementary to a portion of a template is hybridized under appropriate conditions and the polymerase (e.g., DNA polymerase or reverse transcriptase) may then synthesize a nucleic acid molecule complementary to the template or a portion thereof. The newly synthesized molecule, according to the present disclosure, may be equal or shorter in length than the original template. Mismatch incorporation during the synthesis or extension of the newly synthesized molecule may result in one or a number of mismatched base pairs. Thus, the synthesized molecule need not be exactly complementary to the template. The template may be an RNA molecule, a DNA molecule, or a DNA/RNA hybrid molecule. A newly synthesized molecule may serve as a template for subsequent nucleic acid synthesis or amplification.

The target nucleic acid may be a nucleic acid (e.g., DNA or RNA), genomic DNA, cell-free DNA, circulating DNA, cDNA, messenger RNA (mRNA), transfer RNA (tRNA), small interfering RNA (siRNA), microRNA (miRNA), or other mature small RNA, and may comprise nucleic acid analogs or other nucleic acid mimics. The target may be methylated, non-methylated, or both. The target may be bisulfate-treated and non-methylated cytosines converted to uracil. Further, it will be appreciated that "target nucleic acid" may refer to the target nucleic acid itself, as well as surrogates thereof, for example, amplification products and native sequences.

The target nucleic acid may be obtained from any source, and may comprise any number of different compositional components. The target molecules of the present teachings may be derived from any number of sources, including without limitation, viruses, archae, protists, prokaryotes and eukaryotes, for example, from a biological sample obtained from a eukaryotic organism, most preferably a mammal such as a primate e.g., chimpanzee or human. It will be appreciated that target nucleic acids may be isolated from biological samples using any of a variety of procedures known in the art, for example, MagMAX™ DNA Multi-Sample Ultra Kit (Applied Biosystems, Thermo Fisher Scientific), the Mag-MAX™ Express-96 Magnetic Particle Processor and the KingFisher™ Flex Magnetic Particle Processor (Thermo Fisher Scientific), a RecoverAll™ Total Nucleic Acid Isolation Kit for FFPE and PureLink™ FFPE RNA Isolation Kit (Ambion™, Thermo Fisher Scientific), the ABI Prism™ 6100 Nucleic Acid PrepStation and the ABI Prism™ 6700 Automated Nucleic Acid Workstation (Applied Biosystems, Thermo Fisher Scientific), and the like. It will be appreciated that target nucleic acids may be cut or sheared prior to analysis, including the use of such procedures as mechanical force, sonication, restriction endonuclease cleavage, or any method known in the art. In general, the target nucleic acids of the present teachings will be single-stranded, though in some embodiments the target nucleic acids may be double-stranded, and a single-strand may result from denaturation.

The term "incorporating" as used herein, means becoming a part of a DNA or RNA molecule or primer.

The term "nucleic acid binding dye" as used herein refers to a fluorescent molecule that is specific for a double-stranded polynucleotide or that at least shows a substantially greater fluorescent enhancement when associated with double-stranded polynucleotides than with a single stranded polynucleotide. Typically, nucleic acid binding dye molecules associate with double-stranded segments of polynucleotides by intercalating between the base pairs of the double-stranded segment, but binding in the major or minor grooves of the double-stranded segment, or both. Non-limiting examples of nucleic acid binding dyes include ethidium bromide, DAPI, Hoechst derivatives including without limitation Hoechst 33258 and Hoechst 33342, intercalators comprising a lanthanide chelate (for example, but not limited to, a naphthalene diimide derivative carrying two fluorescent tetradentate β-diketone-$Eu^{3+}$ chelates (NDI-(BHHCT-$Eu^{3+}$)$_2$), see e.g., Nojima et al., *Nucl. Acids Res.* Suppl. No. 1 105 (2001), and dertain unsymmetrical cyanine dyes such as SYBR® Green and PicoGreen®.

As used herein, the terms "polynucleotide", "oligonucleotide," and "nucleic acid" are used interchangeably and refer to single-stranded and double-stranded polymers of nucleotide monomers, including without limitation, 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and may include nucleotide analogs. The nucleotide monomer units may comprise any of the nucleotides described herein, including, but not limited to, nucleotides and/or nucleotide analogs. Polynucleotides typically range in size from a few monomeric units, e.g., 5-40 when they are sometimes referred to in the art as oligonucleotides, to several thousands of monomeric nucleotide units. Unless denoted otherwise, whenever a polynucleotide sequence is represented, it will be understood that the nucleotides are in the 5'-to-3' order from left to right and that "A" denotes deoxyadenosine, "C" denotes deoxycytosine, "G" denotes deoxyguanosine, "T" denotes deoxythymidine, and "U" denotes deoxyuridine, unless otherwise noted.

The term "nucleotide" refers to a phosphate ester of a nucleoside, e.g., triphosphate esters, wherein the most common site of esterification is the hydroxyl group attached at the C-5 position of the pentose.

The term "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms. When the nucleoside base is purine or 7-deazapurine, the pentose is attached to the nucleobase at the 9-position of the purine or deazapurine, and when the nucleobase is purimidine, the pentose is attached to the nucleobase at the 1-position of the pyrimidine.

The term "analog" includes synthetic analogs having modified base moieties, modified sugar moieties, and/or modified phosphate ester moieties. Phosphate analogs generally comprise analogs of phosphate wherein the phosphorous atom is in the +5 oxidation state and one or more of the oxygen atoms are replaced with a non-oxygen moiety, e.g. sulfur. Exemplary phosphate analogs include: phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$. Exemplary base analogs include: 2,6-diaminopurine, hypoxanthine, pseudouridine, C-5-propyne, isocytosine, isoguanine, 2-thiopyrimidine. Exemplary sugar analogs include: 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, and bromo.

As used herein, the term "reaction vessel" generally refers to any container, chamber, device, or assembly, in which a reaction can occur in accordance with the present teachings. In some embodiments, a reaction vessel may be a microtube, for example, but not limited to, a 0.2 mL or a 0.5 mL reaction tube such as a MicroAmp™ Optical tube (Life Technologies Corp., Carlsbad, CA) or a micro-centrifuge tube, or other containers of the sort in common practice in molecular biology laboratories. In some embodiments, a reaction vessel comprises a well of a multi-well plate (such as a 48-, 96-, or 384-well microtiter plate), a spot on a glass slide, a well in a TaqMan™ Array Card or a channel or chamber of a microfluidics device, including without limitation a TaqMan™ Low Density Array, or a through-hole of a TaqMan™ OpenArray™ Real-Time PCR plate (Applied Biosystems, Thermo Fisher Scientific). For example, but not as a limitation, a plurality of reaction vessels can reside on the same support. An OpenArray™ Plate, for example, is a reaction plate 3072 through-holes. Each such through-hole in such a plate may contain a single TaqMan™ assay. In some embodiments, lab-on-a-chip-like devices available, for example, from Caliper or Fluidigm can provide reaction vessels. It will be recognized that a variety of reaction vessels are commercially available or can be designed for use in the context of the present teachings.

The term "reporter group" is used in a broad sense herein and refers to any identifiable tag, label, or moiety.

The term "thermostable" when used in reference to an enzyme, refers to an enzyme (such as a polypeptide having nucleic acid polymerase activity) that is resistant to inactivation by heat. A "thermostable" enzyme is in contrast to a "thermolabile" polymerase, which can be inactivated by heat treatment. Thermolabile proteins can be inactivated at physiological temperatures, and can be categorized as meso-thermostable (inactivation at about 45° C. to about 65° C.), and thermostable (inactivation at greater than about 65° C.). For example, the activities of the thermolabile T5 and T7 DNA polymerases can be totally inactivated by exposing the enzymes to a temperature of about 90° C. for about 30 seconds. A thermostable polymerase activity is more resistant to heat inactivation than a thermolabile polymerase. However, a thermostable polymerase does not mean to refer to an enzyme that is totally resistant to heat inactivation; thus heat treatment may reduce the polymerase activity to some extent. A thermostable polymerase typically will also have a higher optimum temperature than thermolabile DNA polymerases.

The term "working concentration" refers to the concentration of a reagent that is at or near the optimal concentration used in a solution to perform a particular function (such as amplification or digestion of a nucleic acid molecule). The working concentration of a reagent is also described equivalently as a "1× concentration" or a "1× solution" (if the reagent is in solution) of the reagent. Accordingly, higher concentrations of the reagent may also be described based on the working concentration; for example, a "2× concentration" or a "2× solution" of a reagent is defined as a concentration or solution that is twice as high as the working concentration of the reagent; a "5× concentration" or a "5× solution" is five times as high as the working concentration, and so on.

The term "amplification reaction mixture" and/or "master mix" may refer to an aqueous solution comprising the various (some or all) reagents used to amplify a target nucleic acid. Such reactions may also be performed using solid supports or semi-solid supports (e.g., an array). The reactions may also be performed in single or multiplex format as desired by the user. These reactions typically include enzymes, aqueous buffers, salts, amplification primers, target nucleic acid, and nucleoside triphosphates. In some embodiments, the amplification reaction mix and/or master mix may include one or more of, for example, a buffer (e.g., Tris), one or more salts (e.g., $MgCl_2$, KO), glycerol, dNTPs (dA, dT, dG, dC, dU), recombinant BSA (bovine serum albumin), a dye (e.g., ROX passive reference dye), one or more detergents, polyethylene glycol (PEG), polyvinyl pyrrolidone (PVP), gelatin (e.g., fish or bovine source) and/or antifoam agent. Depending upon the context, the mixture can be either a complete or incomplete amplification reaction mixture. In some embodiments, the master mix does not include amplification primers prior to use in an amplification reaction. In some embodiments, the master mix does not include target nucleic acid prior to use in an amplification reaction. In some embodiments, an amplification master mix is mixed with a target nucleic acid sample prior to contact with amplification primers.

In some embodiments, the amplification reaction mixture comprises amplification primers and a master mix. In some embodiments, the amplification reaction mixture comprises amplification primers, a detectably labeled probe, and a master mix. In some embodiments, the reaction mixture of amplification primers and master mix or amplification primers, probe and master mix are dried in a storage vessel or reaction vessel. In some embodiments, the reaction mixture of amplification primers and master mix or amplification primers, probe and master mix are lyophilized in a storage vessel or reaction vessel.

In some embodiments, the disclosure generally relates to the amplification of multiple target-specific sequences from a single nucleic acid source or sample. For example, in some embodiments that single nucleic acid sample can include RNA (microbial or otherwise) and in other embodiments, that single nucleic acid sample can include genomic DNA (including microbial genomic DNA). In some embodiments, nucleic acid molecules from at least one other source (e.g., an external control nucleic acid) are combined with the single nucleic acid sample in a reaction mixture prior to the target-specific amplification. It is envisioned that the sample can be from a single individual.

In some embodiments, the target-specific primers and primer pairs are target-specific sequences that can amplify specific regions of a nucleic acid molecule. In some embodiments, the target-specific primers can prime reverse transcription of RNA to generate target-specific cDNA. In some embodiments, the target-specific primers can amplify genomic DNA or cDNA. In some embodiments, the target-specific primers can amplify microbial DNA, such as bacterial DNA, yeast DNA, protozoa DNA, or viral DNA. In some embodiments, the amount of DNA required for selective amplification can be from about 1 ng to 1 microgram. In some embodiments, the amount of DNA required for selective amplification of one or more target sequences can be about 1 ng, about 5 ng or about 10 ng. In some embodiments, the amount of DNA required for selective amplification of target sequence is about 10 ng to about 200 ng.

In one embodiment, a sample containing one or more target sequences can be amplified using any one or more of the target-specific primers disclosed herein. In another embodiment, amplified target sequences obtained using the methods and associated compositions and kits disclosed herein, can be coupled to a downstream process, such as but not limited to, nucleic acid sequencing. For example, once the nucleic acid sequence of an amplified target sequence is known, the nucleic acid sequence can be compared to one or more reference samples. The output from the amplification procedure can be optionally analyzed for example by nucleic acid sequencing to determine if the expected amplification product based on the target-specific primers is present in the amplification output. In some embodiments, amplicons generated by the selective amplification can be cloned prior to sequencing or the amplicons can be sequenced directly without cloning. The amplicons can be sequenced using any suitable DNA sequencing platform. In some embodiments, the amplicons can be sequenced using an Ion Personal Genome Machine™ (PGM™) System or an Ion Proton™ System (Thermo Fisher Scientific).

In some embodiments the length of the amplicon that is produced can be modulated through the use of the selected primer pair. In some aspects, each primer of the set (e.g., the forward primer and the reverse primer) can be configured to specifically hybridize to all or a portion of a different region of a target nucleic acid, such that amplifying the target nucleic acid with the selected primer pair results in an amplicon having a specific size. In some embodiments, the different regions of the target nucleic acid that each primer hybridizes to can be separated by at least 10 nucleotides, at least 20 nucleotides, at least 50 nucleotides, at least 100 nucleotides, at least 250 nucleotides, at least 500 nucleotides, at least 750 nucleotides, etc. Thus, in some embodiments, the selected primer set can produce an amplicon that is at least 10 nucleotides long, at least 20 nucleotides long, at least 50 nucleotides long, at least 100 nucleotides long, at least 250 nucleotides long, at least 500 nucleotides long, at least 750 nucleotides long, etc. In some embodiments, the selected primer pair produces an amplicon that is less than 500 bases in length, less than 300 bases in length, less than 200 bases in length, or less than 100 bases in length. In some embodiments, the amplicon that is produced is between 20 to 500 nucleotides long. For example, the amplicon can be 20 nucleotides long, 50 nucleotides long, 100 nucleotides long, 200 nucleotides long, 300 nucleotides long, 400 nucleotides long, 500 nucleotides long, or any length in between (e.g., any length between and including 20 to 500 nucleotides long). Systems and methods for designing and selecting sets of amplification primers to give a desired amplicon size, for use according to the methods, compositions and kits described herein, are known to those of skill in the art. See, for example, WO2013134341 A1 and ncbi.nlm.nih.gov. Those of skill in the art can also readily determine standard methods for determining amplicon length. For example, in some embodiments, a DNA size marker can be used to demonstrate relative amplicon sizes.

The method used to amplify the target nucleic acid may be any available to one of skill in the art. Any in vitro means for multiplying the copies of a target sequence of nucleic acid may be utilized. These include linear, logarithmic, and/or any other amplification method. While this disclosure may generally discuss PCR as the nucleic acid amplification reaction, it is expected that the modified detergents describe herein should be effective in other types of nucleic acid amplification reactions, including both polymerase-mediated amplification reactions (such as helicase-dependent amplification (HDA), recombinase-polymerase amplification (RPA), and rolling circle amplification (RCA)), as well as ligase-mediated amplification reactions (such as ligase detection reaction (LDR), ligase chain reaction (LCR), and gap-versions of each), and combinations of nucleic acid amplification reactions such as LDR and PCR (see, for example, U.S. Pat. No. 6,797,470). For example, the modified detergents may be used in, for example, various ligation-mediated reactions, where for example ligation probes are employed as opposed to PCR primers. Additional exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (see, e.g., PCT Publication No. WO 2006/081222), strand displacement (see, e.g., U.S. Pat. No. RE39007E), partial destruction of primer molecules (see, e.g., PCT Publication No. WO 2006/087574)), ligase chain reaction (LCR) (see, e.g., Wu, et al., *Genomics* 4: 560-569 (1990)), and/or Barany, et al. *Proc. Natl. Acad. Sci. USA* 88:189-193 (1991)), QI3 RNA replicase systems (see, e.g., PCT Publication No. WO 1994/016108), RNA transcription-based systems (e.g., TAS, 3SR), rolling circle amplification (RCA) (see, e.g., U.S. Pat. No. 5,854,033; U.S. Patent Application Publication No. 2004/265897; Lizardi et al. *Nat. Genet.* 19: 225-232 (1998); and/or Bailer et al. *Nucleic Acid Res.*, 26: 5073-5078 (1998)), and strand displacement amplification (SDA) (Little, et al. *Clin. Chem.* 45:777-784 (1999)), among others. These systems, along with the many other systems available to the skilled artisan, may be suitable for use in polymerizing and/or amplifying target nucleic acids for use as described herein. In certain embodiments, amplification techniques comprise at least one cycle of amplification, for example, but not limited to, the steps of: denaturing a double-stranded nucleic acid to separate the component strands; hybridizing a primer to a target flanking sequence or a primer-binding site of an amplicon (or complements of either, as appropriate); and synthesizing a strand of nucleotides in a template-dependent manner using a DNA polymerase. The cycle may or may not be repeated. In certain embodiments, a cycle of amplification comprises a multiplicity of amplification cycles, for example, but not limited to 20 cycles, 25 cycles, 30 cycles, 35 cycles, 40 cycles, 45 cycles or more than 45 cycles of amplification. In some embodiments, amplifying comprises thermocycling using an instrument, for example, but not limited to, a GeneAmp® PCR System 9700, 9600, 2700 or 2400 thermocycler, an Applied Biosystems® ViiA™ 7 Real-Time PCR System, an Applied Biosystems® 7500 Fast Real-Time PCR System, a 7900HT Fast Real-Time PCR System, a StepOne® Real-Time PCR System, a StepOnePlus® Real-Time PCR System, a QuantStudio™ 12K Flex Real-Time PCR System, a QuantStudio™ Dx Real-Time PCR System and the like (all from Thermo Fisher Scientific). Other examples of spectrophotometric thermal cyclers for use in the methods include, but are not limited to, Bio-Rad ICycler IQ™, Cepheid SmartCycler® II, Corbett Research Rotor-Gene 3000, Idaho Technologies R.A.P.I.D.™, MJ Research Chromo 4™, Roche Applied Science LightCycler®, Roche Applied Science LightCycler®2.0, Stratagene Mx3000P™, and Stratagene Mx4000™. In certain embodiments, single-stranded amplicons are generated in an amplification reaction, for example, but not limited to asymmetric PCR or A-PCR.

The method used to amplify the target nucleic acid may be any available to one of skill in the art. Any in vitro means for multiplying the copies of a target sequence of nucleic acid may be utilized. These include linear, logarithmic, and/or any other amplification method. While this disclosure may generally discuss PCR as the nucleic acid amplification reaction, other types of nucleic acid amplification reactions, including both polymerase-mediated amplification reactions (such as helicase-dependent amplification (HDA), recombinase-polymerase amplification (RPA), and rolling circle amplification (RCA)), as well as ligase-mediated amplification reactions (such as ligase detection reaction (LDR), ligase chain reaction (LCR), and gap-versions of each), and combinations of nucleic acid amplification reactions such as LDR and PCR (see, for example, U.S. Pat. No. 6,797,470) may be suitable. For example, exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (e.g., PCT Publication No. WO 2006/081222), strand displacement (e.g., U.S. Pat. No. RE39007E), partial destruction of primer molecules (e.g., PCT Publication No. WO 2006/087574)), ligase chain reaction (LCR) (e.g., Wu, et al., Genomics 4: 560-569 (1990)), and/or Barany, et al. Proc. Natl. Acad. Sci. USA 88:189-193 (1991)), Qβ RNA replicase systems (e.g., PCT Publication No. WO 1994/016108), RNA transcription-based systems (e.g., TAS, 3SR), rolling circle amplification (RCA) (e.g., U.S. Pat. Nos. 5,854,033 and 7,618,776; Lizardi et al. Nat. Genet. 19: 225-232 (1998); and/or Bailer et al. Nucleic Acid Res., 26: 5073-5078 (1998)), and strand displacement amplification (SDA) (Little, et al. Clin. Chem. 45:777-784 (1999)), among others. These systems, along with the many other systems available to the skilled artisan, may be suitable for use in polymerizing and/or amplifying target nucleic acids for use as described herein.

In some embodiments, one-step RT-PCR is performed in which both the reverse transcription of the target RNA and amplification of the resultant cDNA occurs in the same reaction mixture. In some embodiments, the reaction mixture further includes a detectably labeled, target-specific probe such that detection of the amplified cDNA also occurs in the same reaction mixture.

In some embodiments, amplification comprises a two-step reaction including without limitation, a pre-amplification step wherein a limited number of cycles of amplification occur (for example, but not limited to, 2, 3, 4, or 5 cycles of amplification), then the resulting amplicon is generally diluted and portions of the diluted amplicon are subjected to additional cycles of amplification in a subsequent amplification step (see, e.g., U.S. Pat. No. 6,605,451).

In certain embodiments, an amplification reaction comprises a plurality or multiplicity of single-plex reactions performed in parallel under the same assay conditions and/or at substantially the same time. In some embodiments, performing the plurality of amplification reactions in parallel forms a plurality of different amplification products. In certain embodiments, performing the plurality of amplification reactions in parallel can form between 10 and 10,000 different amplification products. In some embodiments, performing the plurality of amplification reactions in parallel can form between 10 and 1000 different amplification products. In certain embodiments, performing the plurality of amplification reactions in parallel can form between 10 and 100 different amplification products or between 10 and 50 different amplification products.

In certain embodiments, an amplification reaction comprises multiplex amplification, in which a multiplicity of different target nucleic acids and/or a multiplicity of different amplification product species are simultaneously amplified using a multiplicity of different primer sets. In certain embodiments, a multiplex amplification reaction and a single-plex amplification reaction, including a multiplicity of single-plex or lower-plexy reactions (for example, but not limited to a two-plex, a three-plex, a four-plex, a five-plex or a six-plex reaction) are performed in parallel.

As described herein, exemplary methods for polymerizing and/or amplifying nucleic acids include, for example, polymerase-mediated extension reactions. For instance, the polymerase-mediated extension reaction can be the polymerase chain reaction (PCR). In other embodiments, the nucleic acid amplification reaction is a multiplex reaction. For instance, exemplary methods for polymerizing and/or amplifying and detecting nucleic acids suitable for use as described herein are commercially available as TaqMan® assays (see, e.g., U.S. Pat. Nos. 4,889,818; 5,079,352; 5,210,015; 5,436,134; 5,487,972; 5,658,751; 5,210,015; 5,487,972; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and/or 7,445,900, all of which are hereby incorporated herein by reference in their entirety). TaqMan® assays are typically carried out by performing nucleic acid amplification on a target polynucleotide using a nucleic acid polymerase having 5'-to-3' nuclease activity, a primer capable of hybridizing to the target polynucleotide, and an oligonucleotide probe capable of hybridizing to the target polynucleotide 3' relative to the primer. The oligonucleotide probe typically includes a detectable label (e.g., a fluorescent reporter molecule) and a quencher molecule capable of quenching the fluorescence of the reporter molecule. Typically, the detectable label and quencher molecule are part of a single probe. In some embodiments, the detectably labeled probe of the amplification reaction contains a fluorescent label at its 5' end and a quencher at its 3' end. As amplification proceeds, the polymerase digests the probe to separate the detectable label from the quencher molecule. Thus, in some preferred embodiments, the detectably labeled probe of the amplification reaction is configured to undergo cleavage by a polymerase in a 5' nuclease assay (such as in a TaqMan® assay). The detectable label (e.g., fluorescence) is monitored during the reaction, where detection of the label corresponds to the occurrence of nucleic acid amplification (e.g., the higher the signal the greater the amount of amplification). Variations of TaqMan® assays (e.g., LNA™ spiked TaqMan® assay) are known in the art and would be suitable for use in the methods described herein.

In addition to 5'-nuclease probes, such as the probes used in TaqMan® assays, various probes are known in the art and suitable for use in detecting amplified nucleic acids in the provided methods. Exemplary probes include, but are not limited to, various stem-loop molecular beacons (e.g., U.S. Pat. Nos. 6,103,476 and 5,925,517 and Tyagi and Kramer, Nature Biotechnology 14:303-308 (1996)), stemless or linear beacons (e.g., PCT Pub. No. WO 99/21881; U.S. Pat. No. 6,485,901), PNA Molecular Beacons™ (e.g., U.S. Pat. Nos. 6,355,421 and 6,593,091), linear PNA beacons (e.g., Kubista et al., SPIE 4264:53-58 (2001)), non-FRET probes (e.g., U.S. Pat. No. 6,150,097), Sunrise®/Amplifluor® probes (U.S. Pat. No. 6,548,250), stem-loop and duplex Scorpions™ probes (Solinas et al., Nucleic Acids Research 29:E96 (2001) and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes (Svanvik, et al. Anal Biochem 281:26-35 (2000)), self-assembled nanoparticle probes, ferrocene-modified probes described, for example, in U.S. Pat. No. 6,485,901; Mhlanga et al., Methods 25:463-471 (2001); Whitcombe et al., Nature Biotechnology. 17:804-807 (1999); Isacsson et al., Molecular Cell Probes. 14:321-328 (2000); Wolffs et al., Biotechniques 766:769-771 (2001); Tsourkas et al., Nucleic Acids Research. 30:4208-4215 (2002); Riccelli et al., Nucleic Acids Research 30:4088-4093 (2002); Zhang et al., Acta Biochimica et Biophysica Sinica (Shanghai). 34:329-332 (2002); Maxwell et al., J. Am. Chem. Soc. 124:9606-9612 (2002); Broude et al., Trends Biotechnol. 20:249-56 (2002); Huang et al., Chem Res. Toxicol. 15:118-126 (2002); and Yu et al., J. Am. Chem. Soc. 14:11155-11161 (2001); QuantiProbes® (Qiagen), HyBeacons® (French, et al. Mol. Cell. Probes 15:363-374 (2001)), displacement probes (Li, et al. Nucl. Acids Res. 30:e5 (2002)), HybProbes (Cardullo, et al. Proc. Natl. Acad. Sci. USA 85:8790-8794 (1988)), MGB Alert (nanogen.com), Q-PNA (Fiandaca, et al. Genome Res. 11:609-611 (2001)), Plexor™ (Promega), LUX™ primers (Nazarenko, et al. Nucleic Acids Res. 30:e37 (2002)), DzyNA primers (Todd, et al. Clin. Chem. 46:625-630 (2000)). Detectably-labeled probes may also comprise non-detectable quencher moieties that quench the fluorescence of the detectable label, including, for example, black hole quenchers (Biosearch), Iowa Black™ quenchers (IDT), QSY quencher (Molecular Probes™; Thermo Fisher Scientific), and Dabsyl and Dabcyl sulfonate/carboxylate Quenchers (Epoch). Detectably-labeled probes may also comprise two probes, wherein for example a fluorophore is on one probe, and a quencher is on the other, wherein hybridization of the two probes together on a target quenches the signal, or wherein hybridization on a target alters the signal signature via a change in fluorescence. Exemplary systems may also include FRET, salicylate/DTPA ligand systems (Oser et al. Angew. Chem. Int. Engl. 29(10):1167 (1990)), displacement hybridization, homologous probes, and/or assays described in European Pat. No. EP 070685 and/or U.S. Pat. No. 6,238,927. Detectable labels can also comprise sulfonate derivatives of fluorescein dyes with SO3 instead of the carboxylate group, phosphoramidite forms of fluorescein, phosphoramidite forms of Cy5 (available for example from Amersham). All references cited above are hereby incorporated herein by reference in their entirety.

As described herein, one or more detectable labels and/or quenching agents may be attached to one or more primers and/or probes (e.g., detectable label). The detectable label may emit a signal when free or when bound to one of the target nucleic acids. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As described herein, in some embodiments the detectable label may be attached to a probe, which may be incorporated into a primer, or may otherwise bind to amplified target nucleic acid (e.g., a detectable nucleic acid binding agent such as an intercalating or non-intercalating dye). When using more than one detectable label, each should differ in their spectral properties such that the labels may be distinguished from each other, or such that together the detectable labels emit a signal that is not emitted by either detectable label alone. Exemplary detectable labels include, for instance, a fluorescent dye or fluorophore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluoresceins (e.g., 5-carboxy-2,7-dichlorofluorescein; 5-Carboxyfluorescein (5-FAM); 5-Hydroxy Tryptamine (5-HAT); 6-JOE; 6-carboxyfluorescein (6-FAM); FITC; 6-carboxy-1,4-dichloro-2',7'-dichlorofluorescein (TET); 6-carboxy-1,4-dichloro-2',4',5',7'-tetrachlorofluorescein (HEX); 6-carboxy-4',5'-dichloro-2',7'-dimethoxyfluorescein (JOE); Alexa Fluor® fluorophores (e.g., 350, 405, 430, 488, 500, 514, 532, 546, 555, 568, 594, 610, 633, 635, 647, 660, 680, 700, 750); BODIPY™ fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP. EGFP), blue fluorescent protein (e.g., BFP, EBFP, EBFP2, Azurite, mKalamal), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY® FL/BODIPY® FL, Fluorescein/QSY7 and QSY9), LysoTracker® and LysoSensor™ (e.g., LysoTracker® Blue DND-22, LysoTracker® Blue-White DPX, LysoTracker® Yellow HCK-123, LysoTracker® Green DND-26, LysoTracker® Red DND-99, LysoSensor™ Blue DND-167, LysoSensor™ Green DND-189, LysoSensor™ Green DND-153, LysoSensor™ Yellow/Blue DND-160, LysoSensor™ Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, ROX (6-carboxy-X-rhodamine), 5-ROX (carboxy-X-rhodamine), Sulphorhodamine B can C, Sulphorhodamine G Extra, TAMRA (6-carboxytetramethylrhodamine), Tetramethylrhodamine (TRITC), WT), Texas Red, Texas Red-X, VIC and other labels described in, e.g., U.S. Pat. Application Pub. No. 2009/0197254 (incorporated herein by reference in its entirety), among others as would be known to those of skill in the art. Other detectable labels may also be used (see, e.g., U.S. Pat. Application Pub. No. 2009/0197254 (incorporated herein by reference in its entirety)), as would be known to those of skill in the art. Any of these systems and detectable labels, as well as many others, may be used to detect amplified target nucleic acids.

As used herein, the term "detectable label" refers to any of a variety of signaling molecules indicative of amplification. In some embodiments, the reaction mixture may include a detectable label such as SYBR® Green and/or other DNA-binding dyes. Such detectable labels may comprise or may be, for example, nucleic acid intercalating agents or non-intercalating agents. As used herein, an intercalating agent is an agent or moiety capable of non-covalent insertion between stacked base pairs of a double-stranded nucleic acid molecule. A non-intercalating agent is one that does not insert into the double-stranded nucleic acid molecule. The nucleic acid binding agent may produce a detectable signal directly or indirectly. The signal may be detectable directly using, for example, fluorescence and/or absorbance, or indirectly using, for example, any moiety or ligand that is detectably affected by proximity to double-stranded nucleic As used herein, an intercalating agent is an agent or moiety capable of non-covalent insertion between stacked base pairs of a double-stranded nucleic acid molecule. A non-intercalating agent acid is suitable such as a substituted label moiety or binding ligand attached to the nucleic acid binding agent. It is typically necessary for the nucleic acid binding agent to produce a detectable signal when bound to a double-stranded nucleic acid that is distinguishable from the signal produced when that same agent is in solution or bound to a single-stranded nucleic acid. For example, intercalating agents such as ethidium bromide fluoresce more intensely when intercalated into double-stranded DNA than when bound to single-stranded DNA, RNA, or in solution (e.g., U.S. Pat. Nos. 5,994,056; 6,171, 785; and/or 6,814,934). Similarly, actinomycin D fluoresces in the red portion of the UV/VIS spectrum when bound to single-stranded nucleic acids, and fluoresces in the green portion of the UV/VIS spectrum when bound to double-stranded nucleic acids. And in another example, the photo-reactive psoralen 4-aminomethyl-4-5',8-trimethylpsoralen (AMT) has been reported to exhibit decreased absorption at long wavelengths and fluorescence upon intercalation into double-stranded DNA (Johnson et al. Photochem. & Photobiol., 33:785-791 (1981). For example, U.S. Pat. No. 4,257,774 describes the direct binding of fluorescent intercalators to DNA (e.g., ethidium salts, daunomycin, mepacrine and acridine orange, 4',6-diamidino-α-phenylindole). Non-intercalating agents (e.g., minor groove binder moieties (MGBs) as described herein such as Hoechst 33258, distamycin, netropsin) may also be suitable for use. For example, Hoechst 33258 (Searle, et al. Nucl. Acids Res. 18(13):3753-3762 (1990)) exhibits altered fluorescence with an increasing amount of target.

Other DNA binding dyes are available to one of skill in the art and may be used alone or in combination with other agents and/or components of an assay system. Exemplary DNA binding dyes may include, for example, acridines (e.g., acridine orange, acriflavine), actinomycin D (Jain, et al. J. Mol. Biol. 68:21 (1972)), anthramycin, BOBO™-1, BOBO™-3, BO-PRO™-1, cbromomycin, DAPI (Kapuseinski, et al. Nucl. Acids Res. 6(112): 3519 (1979)), daunomycin, distamycin (e.g., distamycin D), dyes described in U.S. Pat. No. 7,387,887, ellipticine, ethidium salts (e.g., ethidium bromide), fluorcoumanin, fluorescent intercalators as described in U.S. Pat. No. 4,257,774, GelStar® (Lonza), Hoechst 33258 (Searle and Embrey, Nucl. Acids Res. 18:3753-3762 (1990)), Hoechst 33342, homidium, JO-PRO™-1, LIZ dyes, LO-PRO™-1, mepacrine, mithramycin, NED dyes, netropsin, 4',6-diamidino-α-phenylindole, proflavine, POPO™-1, POPO™-3, PO-PRO™-1, propidium iodide, ruthenium polypyridyls, S5, SYBR® Gold, SYBR® Green I (U.S. Pat. Nos. 5,436,134 and 5,658,751), SYBR® Green II, SYTOX® blue, SYTOX® green, SYTO® 43, SYTO® 44, SYTO® 45, SYTOX® Blue, TO-PRO®-1, SYTO® 11, SYTO® 13, SYTO® 15, SYTO® 16, SYTO® 20, SYTO® 23, thiazole orange (Sigma-Aldrich Chemical Co.), TOTO™-3, YO-PRO®-1, and YOYO®-3 (Molecular Probes; Thermo Fisher Scientific), among others. SYBR® Green I (e.g., U.S. Pat. Nos. 5,436, 134; 5,658,751; and/or 6,569,927), for example, has been used to monitor a PCR reactions. Other DNA binding dyes may also be suitable as would be understood by one of skill in the art.

Enzymes for use in the methods, compositions and kits provided herein may also include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, et al., Science 239:487-491 (1988); U.S. Pat. Nos. 4,889,818 and 4,965,188), Tne DNA polymerase (WO 96/10640), Tma DNA polymerase (U.S. Pat. No. 5,374,553) and mutants, fragments, variants or derivatives thereof (see, e.g., U.S. Pat. Nos. 5,948,614 and 6,015,668, which are incorporated by reference herein in their entireties). As will be understood by one of ordinary skill in the art, modified reverse transcriptases and DNA polymerase having reverse transcriptase activity may be obtained by recombinant or genetic engineering techniques that are well-known in the art. Mutant reverse transcriptases or polymerases may, for example, be obtained by mutating the gene or genes encoding the reverse transcriptase or polymerase of interest by site-directed or random mutagenesis. Such mutations may include point mutations, deletion mutations and insertional mutations. In some embodiments, one or more point mutations (e.g., substitution of one or more amino acids with one or more different amino acids) are used to construct mutant reverse transcriptases or polymerases for use in the invention. Fragments of reverse transcriptases or polymerases may also be obtained by deletion mutation by recombinant techniques that are well-known in the art, or by enzymatic digestion of the reverse transcriptase(s) or polymerase(s) of interest using any of a number of well-known proteolytic enzymes.

Exemplary polypeptides having reverse transcriptase activity for use in the methods provided herein include Moloney Murine Leukemia Virus (M-MLV) reverse transcriptase, Rous Sarcoma Virus (RSV) reverse transcriptase, Avian Myeloblastosis Virus (AMV) reverse transcriptase, Rous Associated Virus (RAV) reverse transcriptase, Myeloblastosis Associated Virus (MAV) reverse transcriptase and Human Immunodeficiency Virus (HIV) reverse transcriptase, and others described in WO 98/47921 and derivatives, variants, fragments or mutants thereof, and combinations thereof. In a further embodiment, the reverse transcriptases are reduced or substantially reduced in RNase H activity, and may be selected from the group consisting of M-MLV H− reverse transcriptase, RSV H−reverse transcriptase, AMV H− reverse transcriptase, RAV H− reverse transcriptase, MAV H− reverse transcriptase and HIV H− reverse transcriptase, and derivatives, variants, fragments or mutants thereof, and combinations thereof. Reverse transcriptases of particular interest include AMV RT and M-MLV RT, and optionally AMV RT and M-MLV RT having reduced or substantially reduced RNase H activity (e.g., AMV RT alpha H−/BH+ and M-MLV RT H−). Reverse transcriptases for use in the invention include SuperScript™, SuperScript™ II, ThermoScript™ and ThermoScript™ II available from Invitrogen™ (Thermo Fisher Scientific). See generally, WO 98/47921, U.S. Pat. Nos. 5,244,797 and 5,668,005, the entire contents of each of which are herein incorporated by reference.

Polypeptides having reverse transcriptase activity for use in the methods provided herein may be obtained commercially, for example, from Invitrogen™ (Thermo Fisher Scientific), Pharmacia (Piscataway, N.J.), Sigma (Saint Louis, Mo.) or Boehringer Mannheim Biochemicals (Indianapolis, Ind.). Alternatively, polypeptides having reverse transcriptase activity may be isolated from their natural viral or bacterial sources according to standard procedures for isolating and purifying natural proteins that are well-known to one of ordinary skill in the art (see, e.g., Houts, et al., J. Virol. 29:517 (1979)). In addition, the polypeptides having reverse transcriptase activity may be prepared by recombinant DNA techniques that are familiar to one of ordinary skill in the art (see, e.g., Kotewicz, et al., Nucl. Acids Res. 16:265 (1988); Soltis and Skalka, Proc. Natl. Acad. Sci. USA 85:3372-3376 (1988)).

The nucleic acid polymerases that may be employed in the disclosed nucleic acid amplification reactions may be any that function to carry out the desired reaction including, for example, a prokaryotic, fungal, viral, bacteriophage, plant, and/or eukaryotic nucleic acid polymerase. As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'-to-3' direction. Since DNA polymerase can only add a nucleotide onto a pre-existing 3'-OH group, to begin a DNA synthesis reaction, the DNA polymerase needs a primer to which it can add the first nucleotide. Suitable primers may comprise oligonucleotides of RNA or DNA, or chimeras thereof (e.g., RNA/DNA chimerical primers). The DNA polymerases may be a naturally occurring DNA polymerases or a variant of natural enzyme having the above-mentioned activity. For example, it may include a DNA polymerase having a strand displacement activity, a DNA polymerase lacking 5'-to-3' exonuclease activity, a DNA polymerase having a reverse transcriptase activity, or a DNA polymerase having an endonuclease activity.

Polymerases used in accordance with the present teachings may be any enzyme that can synthesize a nucleic acid molecule from a nucleic acid template, typically in the 5' to 3' direction. Suitable nucleic acid polymerases may also comprise holoenzymes, functional portions of the holoenzymes, chimeric polymerase, or any modified polymerase that can effectuate the synthesis of a nucleic acid molecule. Within this disclosure, a DNA polymerase may also include a polymerase, terminal transferase, reverse transcriptase, telomerase, and/or polynucleotide phosphorylase.

The nucleic acid polymerases used in the methods disclosed herein may be mesophilic or thermophilic. Exemplary mesophilic DNA polymerases include T7 DNA polymerase, T5 DNA polymerase, Klenow fragment DNA polymerase, DNA polymerase III and the like. Non-limiting examples of polymerases may include, for example, T7 DNA polymerase, eukaryotic mitochondrial DNA Polymerase γ, prokaryotic DNA polymerase I, II, III, IV, and/or V; eukaryotic polymerase α, β, γ, δ, ε, ζ, ι, and/or κ; *E. coli* DNA polymerase I; *E. coli* DNA polymerase III alpha and/or epsilon subunits; *E. coli* polymerase IV, *E. coli* polymerase V; *T. aquaticus* DNA polymerase I; *B. stearothermophilus* DNA polymerase I; Euryarchaeota polymerases; terminal deoxynucleotidyl transferase (TdT); *S. cerevisiae* polymerase 4; translesion synthesis polymerases; reverse transcriptase; and/or telomerase. Non-limiting examples of suitable thermostable DNA polymerases that may be used include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium* thermoautotrophicum (Mth) DNA polymerase, *mycobacterium* DNA polymerase (Mtb, Mlep), and mutants, and variants and derivatives thereof (U.S. Pat. Nos. 5,436, 149; 4,889,818; 4,965,188; 5,079,352; 5,614,365; 5,374, 553; 5,270,179; 5,047,342; 5,512,462; WO 92/06188; WO 92/06200; WO 96/10640; Barnes, Gene 112:29-35 (1992); Lawyer, et al., PCR Meth. Appl. 2:275-287 (1993); Flaman, et al., Nucl. Acids Res. 22(15):3259-3260 (1994)). RNA polymerases such as T3, T5 and SP6 and mutants, variants and derivatives thereof may also be used in accordance with the present teachings. Generally, any type I DNA polymerase may be used in accordance with the invention although other DNA polymerases may be used including, but not limited to, type III or family A, B, C etc. DNA polymerases. In addition, any genetically engineered DNA polymerases, any having reduced or insignificant 3'-to-5' exonuclease activity (e.g., SuperScript™ DNA polymerase), and/or genetically engineered DNA polymerases (e.g., those having the active site mutation F667Y or the equivalent of F667Y (e.g., in Tth), AmpliTaq™, ThermoSequenase™), AmpliTaq™ Gold, Platinum™ Taq DNA Polymerase, Therminator I, Therminator II, Therminator III, Therminator Gamma (New England Biolabs, Beverly, MA), and/or any derivatives and fragments thereof, may be used in accordance with the present teachings. Examples of DNA polymerases substantially lacking in 3' exonuclease activity include, but are not limited to, Taq, Tne(exo-), Tma(exo-), Pfu (exo-), Pwo(exo-) and Tth DNA polymerases, and mutants, variants and derivatives thereof. Other nucleic acid polymerases may also be suitable as would be understood by one of skill in the art.

DNA polymerases for use in the methods disclosed herein may be obtained commercially, for example, from Invitrogen™ (Thermo Fisher Scientific), Pharmacia (Piscataway, NJ), Sigma (St. Louis, MO), Boehringer Mannheim, and New England Biolabs (Beverly, MA).

The detection of the signal may be using any reagents or instruments that detect a change in fluorescence from a fluorophore. For example, detection may be performed using any spectrophotometric thermal cycler. Examples of spectrophotometric thermal cyclers include, but are not limited to, Applied Biosystems (AB) PRISM® 7000, AB 7300 real-time PCR system, AB 7500 real-time PCR system, AB PRISM™ 7900HT, Bio-Rad ICycler IQ™, Cepheid SmartCycler® II, Corbett Research Rotor-Gene 3000, Idaho Technologies R.A.P.I.D.™, MJ Research Chromo 4™ Roche Applied Science LightCycler®, Roche Applied Science LightCycler®2.0, Stratagene Mx3000P™, and Stratagene Mx4000™. It should be noted that new instruments are being developed at a rapid rate and any like instruments may be used for the methods.

Kits for performing the methods described herein are also provided. As used herein, the term "kit" refers to a packaged set of related components, typically one or more compounds or compositions. The kit may comprise a pair of oligonucleotides for polymerizing and/or amplifying at least one target nucleic acid from a sample, one or more detergents, a nucleic acid polymerase, and/or corresponding one or more probes labeled with a detectable label. The kit may also include samples containing pre-defined target nucleic acids to be used in control reactions. The kit may also optionally include stock solutions, buffers, enzymes, detectable labels or reagents required for detection, tubes, membranes, and the like that may be used to complete the amplification reaction. In some embodiments, multiple primer sets are included. In one embodiment, the kit may include one or more of, for example, a buffer (e.g., Tris), one or more salts (e.g., KCl), glycerol, dNTPs (dATP, dTTP, dGTP, dCTP, dUTP), ddNTPs (ddATP, ddTTP, ddGTP, ddCTP), recombinant BSA (bovine serum albumin), a dye (e.g., ROX passive reference dye), one or more detergents, polyethylene glycol (PEG), polyvinyl pyrrolidone (PVP), gelatin (e.g., fish or bovine source) and/or antifoam agent. Other embodiments of particular systems and kits are also contemplated which would be understood by one of skill in the art.

While the present teachings have been described in terms of these exemplary embodiments, the skilled artisan will readily understand that numerous variations and modifications of these exemplary embodiments are possible without undue experimentation. All such variations and modifications are within the scope of the current teachings. Aspects of the present teachings may be further understood in light of the following examples, which should not be construed as limiting the scope of the teachings in any way.

EXAMPLES

Panels of TaqMan™ Assays were designed to detect and/or profile microbiota of vaginal and urogenital samples. The panels of assays were designed to discriminate between any combination of 2 to 34 different microorganisms and/or genes which include both commensal and pathogenic microbes associated with the vagina and the urogenital area. The panels include assays to detect the bacteria, fungi, protozoa, and viruses as listed in Table 1. TaqMan™ OpenArray™ plates (Applied Biosystems) for the QuantStudio™ 12K Flex Real-Time PCR System (Applied Biosystems) were pre-spotted with the panel of assays. Each assay included a pair of amplification primers and an oligonucleotide TaqMan™ probe with a detectable label. The pair of amplification primers was specific for a portion of a gene of the microorganism and the probe was specific for the amplicon generated by the primers in an amplification reaction.

Figure 3:
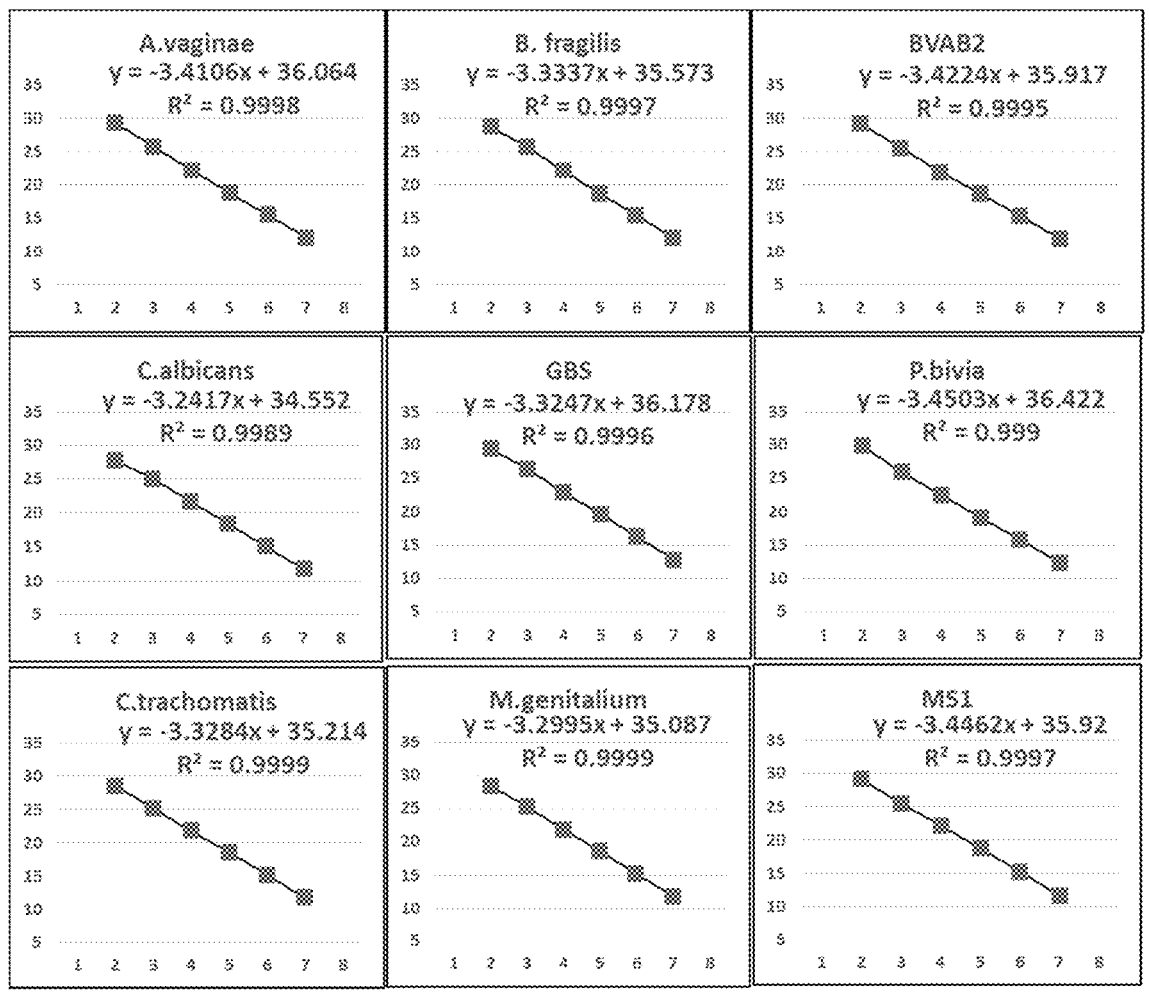
FIG. 3 depicts graphical results for limit of detection and dynamic range for assays directed to a panel of nine different targets. In each graph, the X-axis shows $\log_{10}$ of the template concentration and the Y-axis shows the PCR Ct values.

Limit of Detection (LOD) and dynamic range for the vaginal microbial TaqMan™ assays were examined on OpenArray plates. Plasmid templates containing the amplicon targets were serially diluted across 5 logs from $10^7$ copies per microliter to $10^2$ copies per microliter. A PCR reaction was prepared by adding 2.5 microliters of diluted plasmid template to 2.5 microliters OpenArray PCR master mix for each subarray containing 64 through-holes. Each subarray was spotted with 56 assays and each dilution was run in quadruplicates in 2 different subarrays. The nucleic acid samples and OpenArray PCR master mix were loaded on the OpenArray™ plates using an OpenArray Accufill System and run on the QuantStudio™ 12K Flex system per manufacturer's instructions. All assays showed LOD as low as 100 copies with 5 logs linearity of R2 greater than 0.99. FIG. 1 depicts data from 12 exemplary assays selected to target a panel of the following microbes: *Candida albicans* (CA), *Candida glabrata* (CG). *Candida kruseii* (CK), *Gardnerella vaginalis* (GV), Herpes simplex virus-1 (HSV1), Herpes simplex virus-2 (HSV2), *Lactobacillus iners* (LI), Megasphera 1 (MG1), *Mycoplasma hominis* (MH), *Neisseria gonorrhoeae* (NG), *Trichomonas vaginalis* (TV), and *Ureaplasma urealyticum* (UU). FIG. 3 depicts data from 9 exemplary assays selected to target a panel of the following microbes: *Atopobium vaginae* (A. vaginae), *Bacteroides fragilis* (B fragilis), BVAB2, *Candida albicans* (C. albicans), Group B Strep (GBS), *Prevotella bivia* (P. bivia), *Chlamydia trachomatis* (C trachomatis), *Mycoplasma genitalium* (M genitalium), Megasphera 1 (MS1).

Figures 2A, 2B:
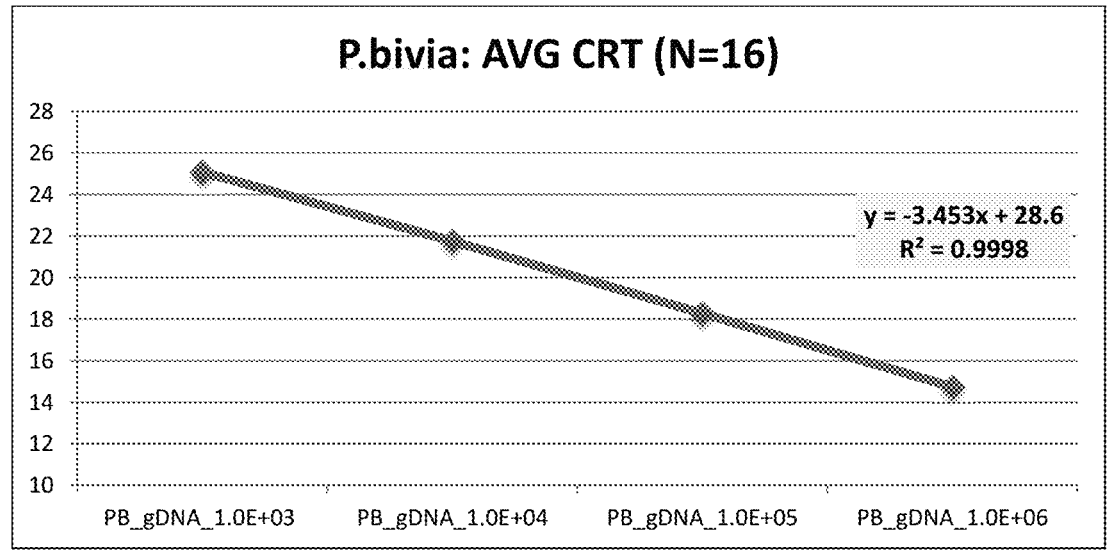
FIG. 2A and FIG. 2B depict results for a *Prevotella bivia* TaqMan™ assay with a sample of *Prevotella bivia* genomic DNA (gDNA). In graph, the X-axis shows the gDNA concentration and the Y-axis shows the PCR Ct values.

A TaqMan assay designed to detect *Prevotella bivia* was performed on a *Prevotella bivia* ATCC gDNA sample. The gDNA sample was serially diluted across 4 logs and the assay was performed on an OpenArray plate as described. FIG. 2 depicts data from the *P. bivia* assay of the gDNA sample. The *P. bivia* assay is specific for *P. bivia* gDNA. No cross-reactivity was observed with the *P. bivia* assay when tested with at least 29 different microorganism gDNA samples.

Nucleic acid extractions were performed on 23 vaginal swab samples using MagMax™ DNA Multi-Sample Ultra Kit reagents and KingFisher™ Flex Purification instrument according to manufacture instructions (Applied Biosystems and Thermo Scientific, Thermo Fisher Scientific). The nucleic acid preparations from the samples underwent multiplex screening with the TaqMan™ assays on OpenArray plates. Pathogens in the vaginal samples had been identified by testing on different platforms prior to the OpenArray screening. Six different samples gave unexpected results with the OpenArray screening (unexpected positives and negatives) based on the prior testing. These six samples with unexpected results were orthogonally profiled via next-generation sequencing (NGS) using Ion AmpliSeq™ reactions on the Ion Torrent Proton™ System (Thermo Fisher Scientific). Results from the NGS testing of these samples with unexpected positives/negatives were in 100% concordance with the OpenArray (OA) results (Table 4).

TABLE 5

| Organism | Sample 1 OA | Sample 1 NGS | Sample 2 OA | Sample 2 NGS | Sample 3 OA | Sample 3 NGS | Sample 4 OA | Sample 4 NGS | Sample 5 OA | Sample 5 NGS | Sample 6 OA | Sample 6 NGS |
|---|---|---|---|---|---|---|---|---|---|---|---|---|
| *Atopobium vaginae* | + | + | | | + | + | + | + | | | + | + |
| *Candida albicans* | | | − | − | + | + | | | | | − | − |
| *Chlamydia trachomatis* | + | + | | | | | | | | | + | + |
| *Gardnerella vaginalis* | | | − | − | + | + | + | + | | | | |
| *Lactobacillus crispatus* | | | + | + | + | + | | | | | | |
| *Lactobacillus gasseri* | | | | | + | + | | | | | | |
| *Lactobacillus iners* | | | | | | | | | + | + | | |
| *Lactobacillus jensenii* | | | | | | | | | + | + | | |
| *Mobiluncus curtisii* | | | | | | | | | | | + | + |
| *Mobiluncus mulieris* | + | + | | | | | + | + | − | − | + | + |
| *Mycoplasma genitalium* | | | | | | | | | | | | |
| *Mycoplasma hominis* | | | | | | | | | | | + | + |
| *Streptococcus agalactiae* | | | − | − | | | | | | | | |
| *Trichomonas vaginalis* | + | + | | | | | | | | | | |
| *Ureaplasma urealyticum* | | | | | | | | | + | + | + | + |

What is claimed is:

1. A method for detecting the presence of nucleic acid of two or more microorganisms in a sample, said method comprising:
   (a) distributing portions of a nucleic acid sample to individual reaction chambers situated within a support;
   (b) performing parallel amplification reactions and forming amplification products in individual reaction chambers, wherein each amplification reaction contains a pair of amplification primers configured to produce an amplification product corresponding to said target nucleic acid sequence present within, or derived from, the genome of each microorganism, wherein said amplification products comprise a first amplification product comprising SEQ ID NO: 20 and one or more additional amplification products comprising one nucleotide sequence selected from SEQ ID NOs: 1-3, 7 or 13; and
   (c) determining whether said amplification products have been formed in one or more of said individual reaction chambers.

2. The method of claim 1, wherein said determining includes detecting hybridization of a detectably labeled probe to said amplification product, optionally in real-time.

3. The method of claim 1, further providing a detectably labeled probe to one or more individual reaction chambers so as to detect an amplification product formed from the amplification reaction(s), wherein the detectably labeled probes includes a sequence that is identical or complementary to a portion of the corresponding target nucleic acid sequence.

4. The method of claim 3, wherein said detectably labeled probe of at least one amplification reaction is configured to undergo cleavage by a polymerase in a 5' nuclease assay.

5. The method of claim 1, comprising preparing said nucleic acid sample from a vaginal swab specimen prior to said distributing.

* * * * *

SEQUENCE LISTING

<160> NUMBER OF SEQ ID NOS: 34

<210> SEQ ID NO 1
<211> LENGTH: 18
<212> TYPE: DNA
<213> ORGANISM: Artificial Sequence
<220> FEATURE:
<223> OTHER INFORMATION: Synthetic DNA

<400> SEQUENCE: 1
gagcgtgtaa ctgttaaa                                                    18

<210> SEQ ID NO 2
<211> LENGTH: 18
<212> TYPE: DNA
<213> ORGANISM: Artificial Sequence
<220> FEATURE:
<223> OTHER INFORMATION: Synthetic DNA

<400> SEQUENCE: 2
tttgcataat gaatctga                                                    18

<210> SEQ ID NO 3
<211> LENGTH: 18
<212> TYPE: DNA
<213> ORGANISM: Artificial Sequence
<220> FEATURE:
<223> OTHER INFORMATION: Synthetic DNA

<400> SEQUENCE: 3
aagtgtgatg tttaaatc                                                    18

<210> SEQ ID NO 4
<211> LENGTH: 18
<212> TYPE: DNA
<213> ORGANISM: Artificial Sequence
<220> FEATURE:
<223> OTHER INFORMATION: Synthetic DNA

<400> SEQUENCE: 4
gacaagaatg cctctgtc                                                    18

<210> SEQ ID NO 5
<211> LENGTH: 18
<212> TYPE: DNA

```
<213> ORGANISM: Artificial Sequence
<220> FEATURE:
<223> OTHER INFORMATION: Synthetic DNA

<400> SEQUENCE: 5
gcctgttgaa atcgcaat                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetic DNA

<400> SEQUENCE: 6
agcgattgaa atttatcc                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetic DNA

<400> SEQUENCE: 7
ggtgaccttc atcgtgct                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetic DNA

<400> SEQUENCE: 8
taggctatca attaaatg                                                 18

<210> SEQ ID NO 9
<211> LENGTH: 18
<212> TYPE: DNA
<213> ORGANISM: Artificial Sequence
<220> FEATURE:
<223> OTHER INFORMATION: Synthetic DNA

<400> SEQUENCE: 9
agttgctatc ggttatcg                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic DNA

<400> SEQUENCE: 10
agttgctatc ggttatcg                                                 18

<210> SEQ ID NO 11
<211> LENGTH: 18
<212> TYPE: DNA
<213> ORGANISM: Artificial Sequence
<220> FEATURE:
<223> OTHER INFORMATION: Synthetic DNA

<400> SEQUENCE: 11
aggtttttta tcatcctt                                                 18
```

```
<210> SEQ ID NO 12
<211> LENGTH: 18
<212> TYPE: DNA
<213> ORGANISM: Artificial Sequence
<220> FEATURE:
<223> OTHER INFORMATION: Synthetic DNA

<400> SEQUENCE: 12
gttatatgtt atttgttg                                                 18

<210> SEQ ID NO 13
<211> LENGTH: 18
<212> TYPE: DNA
<213> ORGANISM: Artificial Sequence
<220> FEATURE:
<223> OTHER INFORMATION: Synthetic DNA

<400> SEQUENCE: 13
ggcgtaaagg gcgcgcag                                                 18

<210> SEQ ID NO 14
<211> LENGTH: 18
<212> TYPE: DNA
<213> ORGANISM: Artificial Sequence
<220> FEATURE:
<223> OTHER INFORMATION: Synthetic DNA

<400> SEQUENCE: 14
acgggacgaa cggcaagg                                                 18

<210> SEQ ID NO 15
<211> LENGTH: 18
<212> TYPE: DNA
<213> ORGANISM: Artificial Sequence
<220> FEATURE:
<223> OTHER INFORMATION: Synthetic DNA

<400> SEQUENCE: 15
acatctgttc caaaatct                                                 18

<210> SEQ ID NO 16
<211> LENGTH: 18
<212> TYPE: DNA
<213> ORGANISM: Artificial Sequence
<220> FEATURE:
<223> OTHER INFORMATION: Synthetic DNA

<400> SEQUENCE: 16
acttgttggg gatactta                                                 18

<210> SEQ ID NO 17
<211> LENGTH: 18
<212> TYPE: DNA
<213> ORGANISM: Artificial Sequence
<220> FEATURE:
<223> OTHER INFORMATION: Synthetic DNA

<400> SEQUENCE: 17
acttccattc caaatctt                                                 18

<210> SEQ ID NO 18
<211> LENGTH: 18
<212> TYPE: DNA
<213> ORGANISM: Artificial Sequence
<220> FEATURE:
```

<223> OTHER INFORMATION: Synthetic DNA

<400> SEQUENCE: 18
tgaattcttt gttagaaa                                                  18

<210> SEQ ID NO 19
<211> LENGTH: 18
<212> TYPE: DNA
<213> ORGANISM: Artificial Sequence
<220> FEATURE:
<223> OTHER INFORMATION: Synthetic DNA

<400> SEQUENCE: 19
gaagtaaaac tgtattac                                                  18

<210> SEQ ID NO 20
<211> LENGTH: 18
<212> TYPE: DNA
<213> ORGANISM: Artificial Sequence
<220> FEATURE:
<223> OTHER INFORMATION: Synthetic DNA

<400> SEQUENCE: 20
ggcaacggtg gcttagtg                                                  18

<210> SEQ ID NO 21
<211> LENGTH: 18
<212> TYPE: DNA
<213> ORGANISM: Artificial Sequence
<220> FEATURE:
<223> OTHER INFORMATION: Synthetic DNA

<400> SEQUENCE: 21
gtataaacga gacacact                                                  18

<210> SEQ ID NO 22
<211> LENGTH: 18
<212> TYPE: DNA
<213> ORGANISM: Artificial Sequence
<220> FEATURE:
<223> OTHER INFORMATION: Synthetic DNA

<400> SEQUENCE: 22
gaaacagata cgacgtgg                                                  18

<210> SEQ ID NO 23
<211> LENGTH: 18
<212> TYPE: DNA
<213> ORGANISM: Artificial Sequence
<220> FEATURE:
<223> OTHER INFORMATION: Synthetic DNA

<400> SEQUENCE: 23
gtgaactccg tattgaag                                                  18

<210> SEQ ID NO 24
<211> LENGTH: 18
<212> TYPE: DNA
<213> ORGANISM: Artificial Sequence
<220> FEATURE:
<223> OTHER INFORMATION: Synthetic DNA

<400> SEQUENCE: 24
tttgatgatc ctgacata                                                  18

```
<210> SEQ ID NO 25
<211> LENGTH: 18
<212> TYPE: DNA
<213> ORGANISM: Artificial Sequence
<220> FEATURE:
<223> OTHER INFORMATION: Synthetic DNA

<400> SEQUENCE: 25
gtggagtttt aactcatt                                                 18

<210> SEQ ID NO 26
<211> LENGTH: 18
<212> TYPE: DNA
<213> ORGANISM: Artificial Sequence
<220> FEATURE:
<223> OTHER INFORMATION: Synthetic DNA

<400> SEQUENCE: 26
aaactgatgg cgattatg                                                 18

<210> SEQ ID NO 27
<211> LENGTH: 18
<212> TYPE: DNA
<213> ORGANISM: Artificial Sequence
<220> FEATURE:
<223> OTHER INFORMATION: Synthetic DNA

<400> SEQUENCE: 27
ccaccacaac ttcagatt                                                 18

<210> SEQ ID NO 28
<211> LENGTH: 18
<212> TYPE: DNA
<213> ORGANISM: Artificial Sequence
<220> FEATURE:
<223> OTHER INFORMATION: Synthetic DNA

<400> SEQUENCE: 28
ttcagggacg cttggcgg                                                 18

<210> SEQ ID NO 29
<211> LENGTH: 18
<212> TYPE: DNA
<213> ORGANISM: Artificial Sequence
<220> FEATURE:
<223> OTHER INFORMATION: Synthetic DNA

<400> SEQUENCE: 29
gtcgaactga tggtggcc                                                 18

<210> SEQ ID NO 30
<211> LENGTH: 18
<212> TYPE: DNA
<213> ORGANISM: Artificial Sequence
<220> FEATURE:
<223> OTHER INFORMATION: Synthetic DNA

<400> SEQUENCE: 30
agatggaaca ccaacact                                                 18

<210> SEQ ID NO 31
<211> LENGTH: 18
<212> TYPE: DNA
<213> ORGANISM: Artificial Sequence
<220> FEATURE:
<223> OTHER INFORMATION: Synthetic DNA
```

```
-continued

<400> SEQUENCE: 31
gtgatacatg gtaagaaa                                                 18

<210> SEQ ID NO 32
<211> LENGTH: 18
<212> TYPE: DNA
<213> ORGANISM: Artificial Sequence
<220> FEATURE:
<223> OTHER INFORMATION: Synthetic DNA

<400> SEQUENCE: 32
gctgctgaat cagtcgaa                                                 18

<210> SEQ ID NO 33
<211> LENGTH: 18
<212> TYPE: DNA
<213> ORGANISM: Artificial Sequence
<220> FEATURE:
<223> OTHER INFORMATION: Synthetic DNA

<400> SEQUENCE: 33
acaggaggtc agtgtctg                                                 18

<210> SEQ ID NO 34
<211> LENGTH: 18
<212> TYPE: DNA
<213> ORGANISM: Artificial Sequence
<220> FEATURE:
<223> OTHER INFORMATION: Synthetic DNA

<400> SEQUENCE: 34
cgggatagcg tcttgttg                                                 18
```